(12) United States Patent
Forsell

(10) Patent No.: US 11,660,562 B2
(45) Date of Patent: May 30, 2023

(54) DRAINAGE DEVICE COMPRISING A FILTER CLEANING DEVICE

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 155 days.

(21) Appl. No.: 17/348,792

(22) Filed: Jun. 16, 2021

(65) Prior Publication Data

US 2021/0308434 A1   Oct. 7, 2021

Related U.S. Application Data

(63) Continuation of application No. 15/730,768, filed on Oct. 12, 2017, now Pat. No. 11,045,631, which is a
(Continued)

(51) Int. Cl.
*A61M 27/00* (2006.01)
*A61M 1/00* (2006.01)
*A61M 60/50* (2021.01)
*A61M 60/857* (2021.01)
*A61M 60/871* (2021.01)
(Continued)

(52) U.S. Cl.
CPC ............ *B01D 46/68* (2022.01); *A61F 2/0036* (2013.01); *A61M 1/71* (2021.05); *A61M 1/72* (2021.05); *A61M 1/79* (2021.05); *A61M 1/82* (2021.05); *A61M 27/002* (2013.01); *A61M 60/50* (2021.01); *A61M 60/857* (2021.01); *A61M 60/871* (2021.01); *B01D 46/681* (2022.01); *A61F 2/482* (2021.08); *A61F 2/484* (2021.08); *A61F 2250/0001* (2013.01); *A61F 2250/0002* (2013.01); *A61M 27/006* (2013.01); *A61M 60/00* (2021.01); *A61M 60/122* (2021.01); *A61M 2027/004* (2013.01); *A61M 2205/10* (2013.01); *A61M 2205/3331* (2013.01); *A61M 2205/3523* (2013.01); *A61M 2210/1021* (2013.01); *A61M 2210/1078* (2013.01); *B01D 46/66* (2022.01);
(Continued)

(58) Field of Classification Search
CPC ............ B01D 46/0057; B01D 46/0065; B01D 46/0064; A61M 1/02; A61M 1/0218; A61M 1/0222; A61M 1/0281; A61M 1/14; A61M 1/1678; A61M 1/34; A61M 2202/005; A61M 2205/7563; A61M 2205/7554
See application file for complete search history.

(56) References Cited

U.S. PATENT DOCUMENTS 3,906,674 A * 9/1975 Stone ........................ B24C 9/00
                                                                451/89
4,509,947 A * 4/1985 Lattin ................... H01L 41/087
                                                                604/20
(Continued)

*Primary Examiner* — Guy K Townsend

(57) ABSTRACT

The present invention relates to a filtering device for removing particles from a bodily fluid of a patient, the filtering device being implantable in the patient's body. The device has a tube forming a main fluid passageway for bodily fluid, through which the bodily fluid of the patient passes when the tube is implanted in the patient, a filter connected to the tube and a filter cleaning device for cleaning the filter by moving particles collected by the filter out of the fluid passageway, wherein the filter cleaning device is adapted to replace the first filter in the fluid passageway with a second filter, thereby moving the particles collected by the first filter out of the fluid passageway.

20 Claims, 24 Drawing Sheets

Related U.S. Application Data continuation of application No. 12/864,695, filed as application No. PCT/SE2009/000036 on Jan. 28, 2009, now Pat. No. 9,789,290.

(60) Provisional application No. 61/006,711, filed on Jan. 28, 2008.

(51) Int. Cl.

| | | |
|---|---|---|
| *B01D 46/00* | (2022.01) | |
| *B01D 46/68* | (2022.01) | |
| *A61F 2/00* | (2006.01) | |
| *B01D 46/681* | (2022.01) | |
| *A61F 2/48* | (2006.01) | |
| *B01D 46/66* | (2022.01) | |
| *B01D 46/79* | (2022.01) | |
| *B01D 46/86* | (2022.01) | |
| *B01D 46/88* | (2022.01) | |
| *B01D 46/90* | (2022.01) | |
| *A61M 60/122* | (2021.01) | |
| *A61M 60/00* | (2021.01) | |

(52) U.S. Cl.
CPC ............ *B01D 46/79* (2022.01); *B01D 46/86* (2022.01); *B01D 46/88* (2022.01); *B01D 46/90* (2022.01)

(56) References Cited

U.S. PATENT DOCUMENTS

| | | | | |
|---|---|---|---|---|
| 4,568,851 A * | 2/1986 | Soni | H01L 41/087 | 310/330 |
| 4,698,058 A * | 10/1987 | Greenfeld | A61M 25/0017 | 604/266 |
| 4,771,772 A * | 9/1988 | DeWitt | A61N 1/375 | 604/266 |
| 4,950,224 A * | 8/1990 | Gorsuch | A61M 1/1643 | 604/6.04 |
| 5,151,082 A * | 9/1992 | Gorsuch | A61M 1/1643 | 210/645 |
| 5,152,743 A * | 10/1992 | Gorsuch | A61B 5/14528 | 604/6.09 |
| 5,194,145 A * | 3/1993 | Schoendorfer | B01D 61/025 | 210/651 |
| 5,224,926 A * | 7/1993 | Gorsuch | A61B 5/14528 | 604/6.04 |
| 5,397,354 A * | 3/1995 | Wilk | A61M 5/14276 | 623/23.65 |
| 5,735,809 A * | 4/1998 | Gorsuch | B01D 63/024 | 604/6.04 |
| 5,738,792 A * | 4/1998 | Schoendorfer | A61M 1/3496 | 210/651 |
| 5,800,457 A * | 9/1998 | Gelbfish | A61F 2/0105 | 606/200 |
| 5,980,478 A * | 11/1999 | Gorsuch | A61M 1/3479 | 604/408 |
| 6,007,607 A * | 12/1999 | Becker | D01G 15/82 | 55/296 |
| 6,022,333 A * | 2/2000 | Kensey | A61M 1/28 | 604/29 |
| 6,099,495 A * | 8/2000 | Kinghorn | A61M 5/14276 | 604/93.01 |
| 6,132,415 A * | 10/2000 | Finch | A61M 1/81 | 604/93.01 |
| 6,183,450 B1 * | 2/2001 | Lois | A61M 25/00 | 604/164.01 |
| 6,254,567 B1 * | 7/2001 | Treu | A61M 1/284 | 604/29 |
| 6,311,905 B1 * | 11/2001 | Galanty | B02C 18/24 | 241/46.06 |
| 6,659,973 B2 * | 12/2003 | Gorsuch | A61M 1/1688 | 604/4.01 |
| 6,849,183 B2 * | 2/2005 | Gorsuch | A61M 1/3431 | 210/321.71 |
| 7,186,290 B2 * | 3/2007 | Sheehan | B01D 46/0028 | 55/497 |
| 7,686,825 B2 * | 3/2010 | Hauser | A61B 17/225 | 606/200 |
| 7,909,790 B2 * | 3/2011 | Burnett | A61M 27/006 | 604/9 |
| 9,789,290 B2 * | 10/2017 | Forsell | A61M 60/857 | |
| 10,384,042 B2 * | 8/2019 | Forsell | A61M 60/50 | |
| 10,441,398 B2 * | 10/2019 | Forsell | A61M 1/782 | |
| 11,045,631 B2 * | 6/2021 | Forsell | A61M 1/72 | |
| 2002/0008068 A1 * | 1/2002 | Anderson | B01D 29/684 | 210/741 |
| 2002/0066811 A1 * | 6/2002 | Galanty | B01D 29/76 | 241/46.06 |
| 2002/0087109 A1 * | 7/2002 | Gorsuch | A61M 1/1678 | 604/6.04 |
| 2002/0165575 A1 * | 11/2002 | Saleh | A61F 2/01 | 606/200 |
| 2003/0060695 A1 * | 3/2003 | Connelly | A61B 5/15087 | 600/365 |
| 2003/0163079 A1 * | 8/2003 | Burnett | A61M 27/002 | 604/9 |
| 2003/0236482 A1 * | 12/2003 | Gorsuch | A61M 1/1678 | 604/4.01 |
| 2004/0034317 A1 * | 2/2004 | Gorsuch | A61M 1/1684 | 604/5.02 |
| 2004/0147871 A1 * | 7/2004 | Burnett | A61M 1/28 | 604/9 |
| 2004/0167613 A1 * | 8/2004 | Yodfat | A61F 2/856 | 623/1.35 |
| 2005/0096582 A1 * | 5/2005 | Burnett | A61M 5/14276 | 604/9 |
| 2005/0150382 A1 * | 7/2005 | Sheehan | B01D 46/0028 | 96/429 |
| 2005/0173343 A1 * | 8/2005 | Kiss | A61M 1/1684 | 210/85 |
| 2006/0015138 A1 * | 1/2006 | Gertner | A61F 2/01 | 606/200 |
| 2006/0058731 A1 * | 3/2006 | Burnett | A61M 1/282 | 604/29 |
| 2006/0167539 A1 * | 7/2006 | McEwan | A61B 90/06 | 623/1.35 |
| 2009/0198271 A1 * | 8/2009 | Gross | A61F 2/01 | 606/200 |
| 2009/0254172 A1 * | 10/2009 | Grewe | A61F 2/856 | 623/1.15 |
| 2010/0318116 A1 * | 12/2010 | Forsell | B01D 46/681 | 606/200 |
| 2010/0318117 A1 * | 12/2010 | Forsell | A61M 60/871 | 606/200 |
| 2010/0318118 A1 * | 12/2010 | Forsell | B01D 46/68 | 606/201 |
| 2010/0324591 A1 * | 12/2010 | Forsell | A61M 1/82 | 606/200 |

* cited by examiner

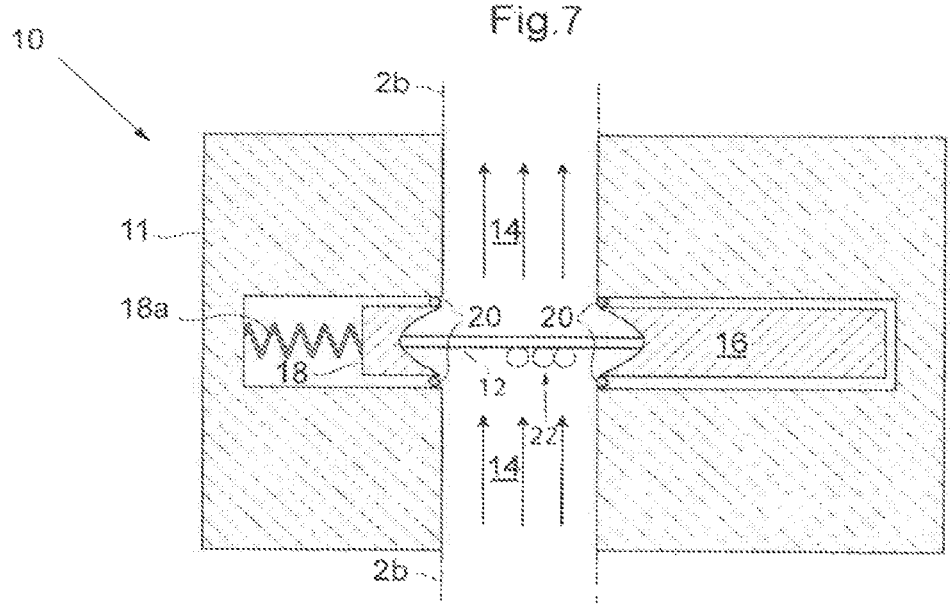
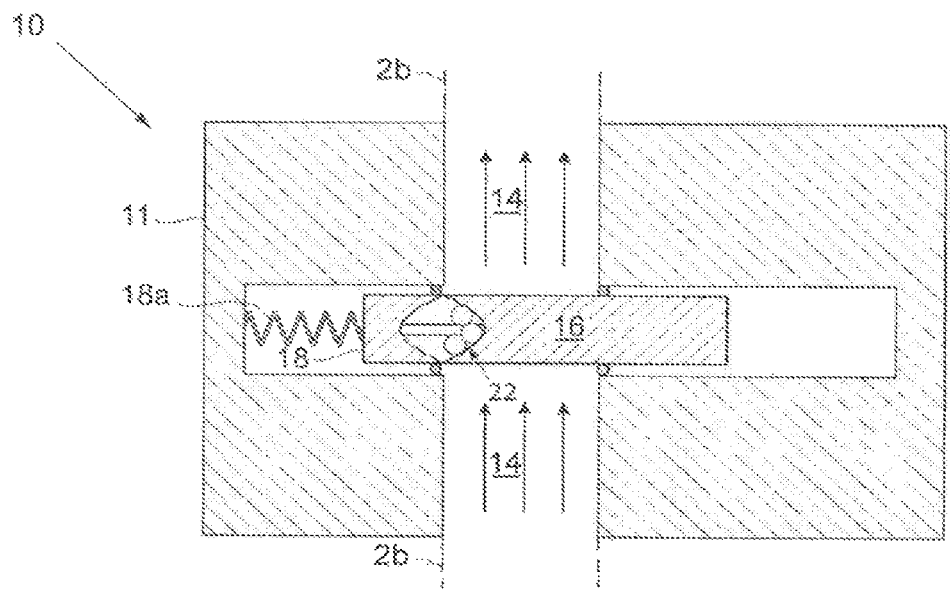

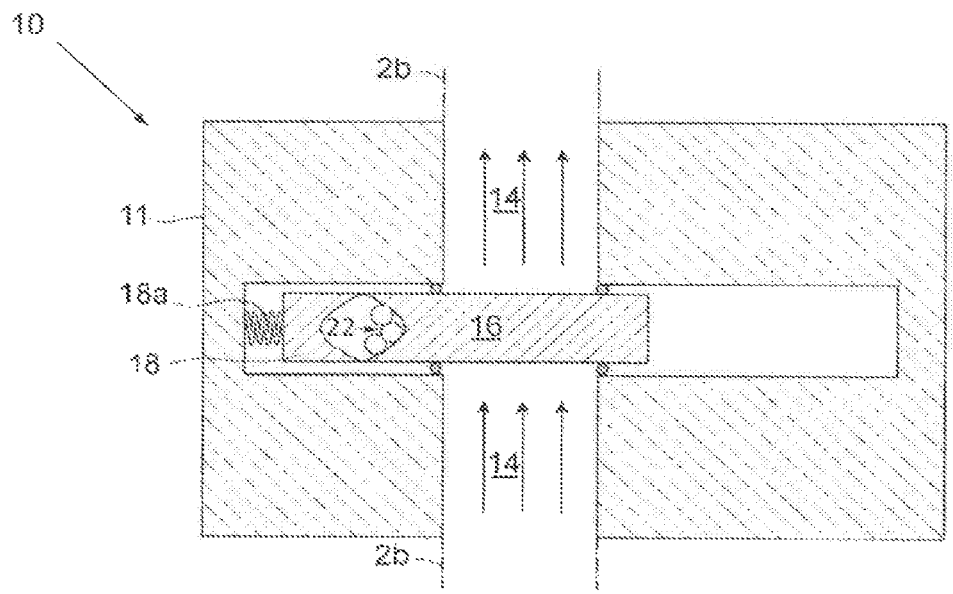
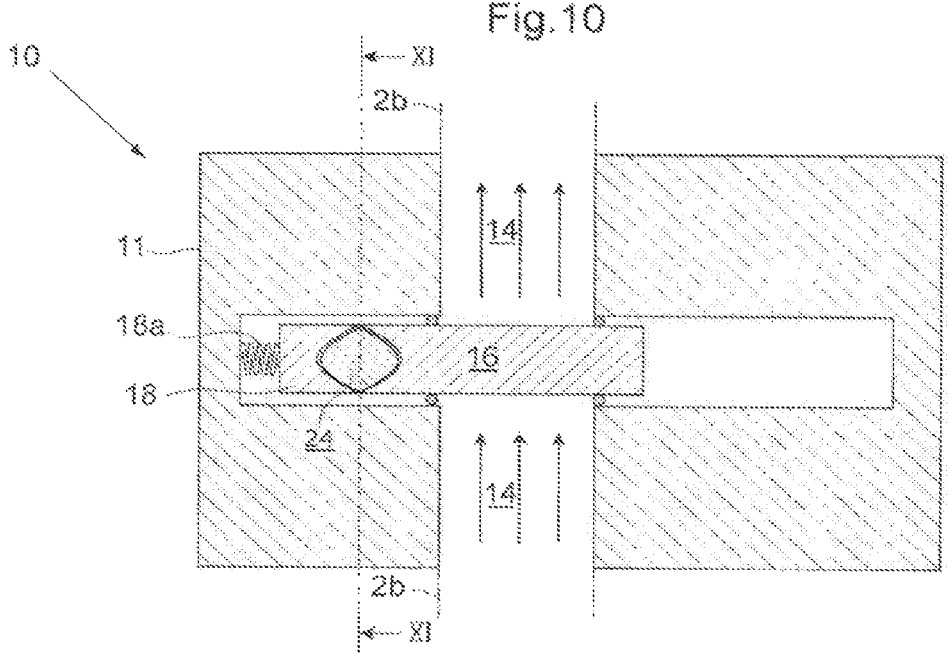

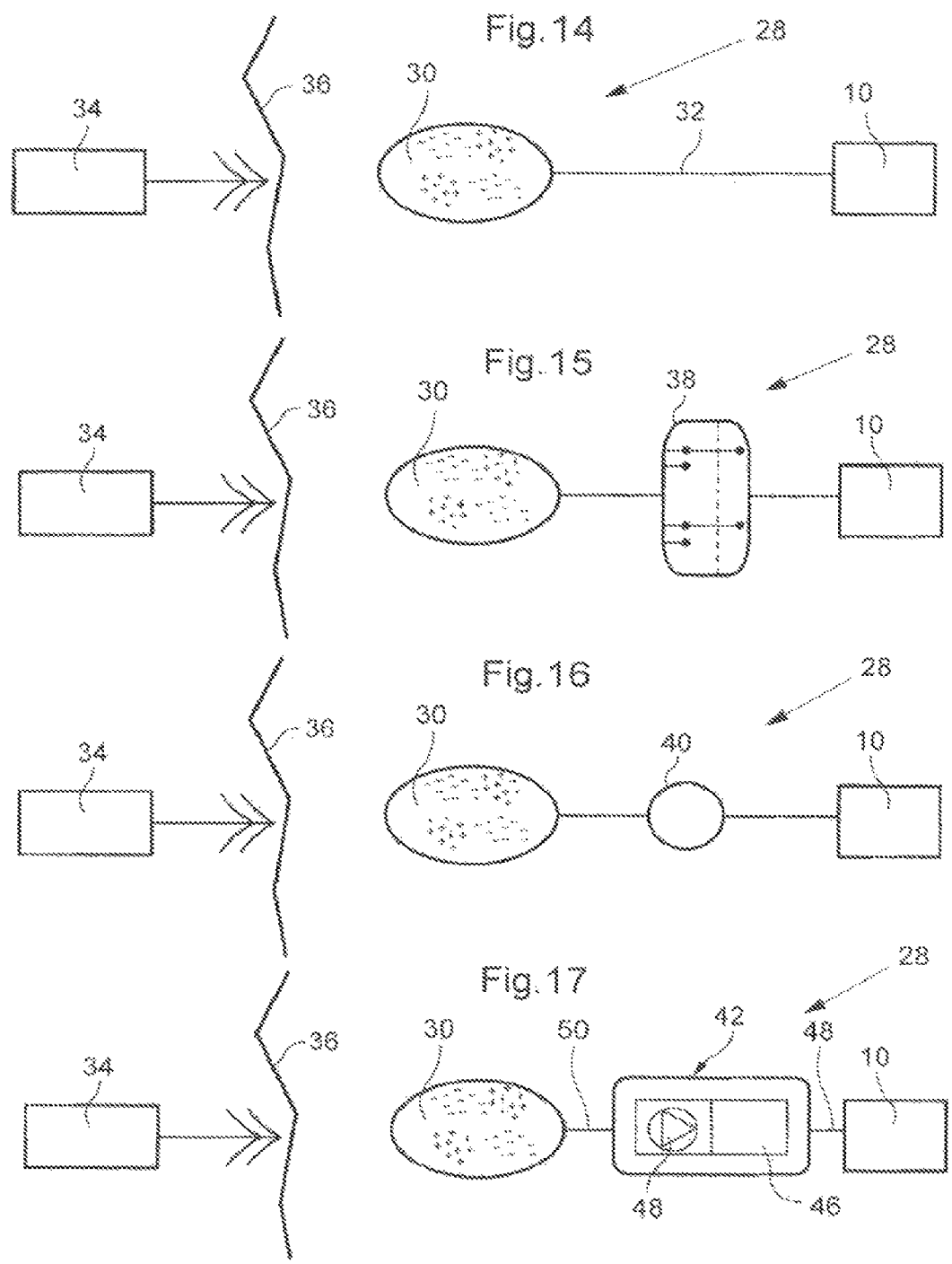

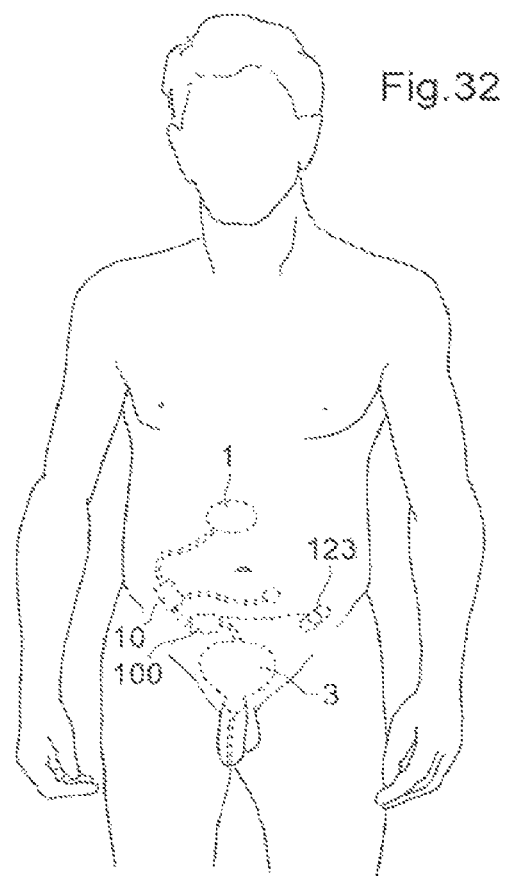
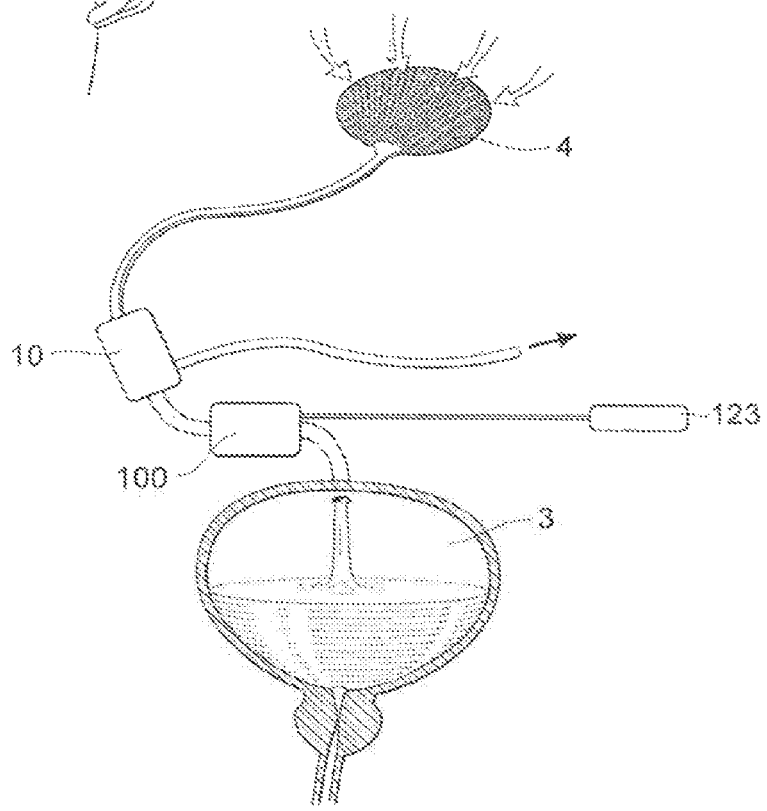

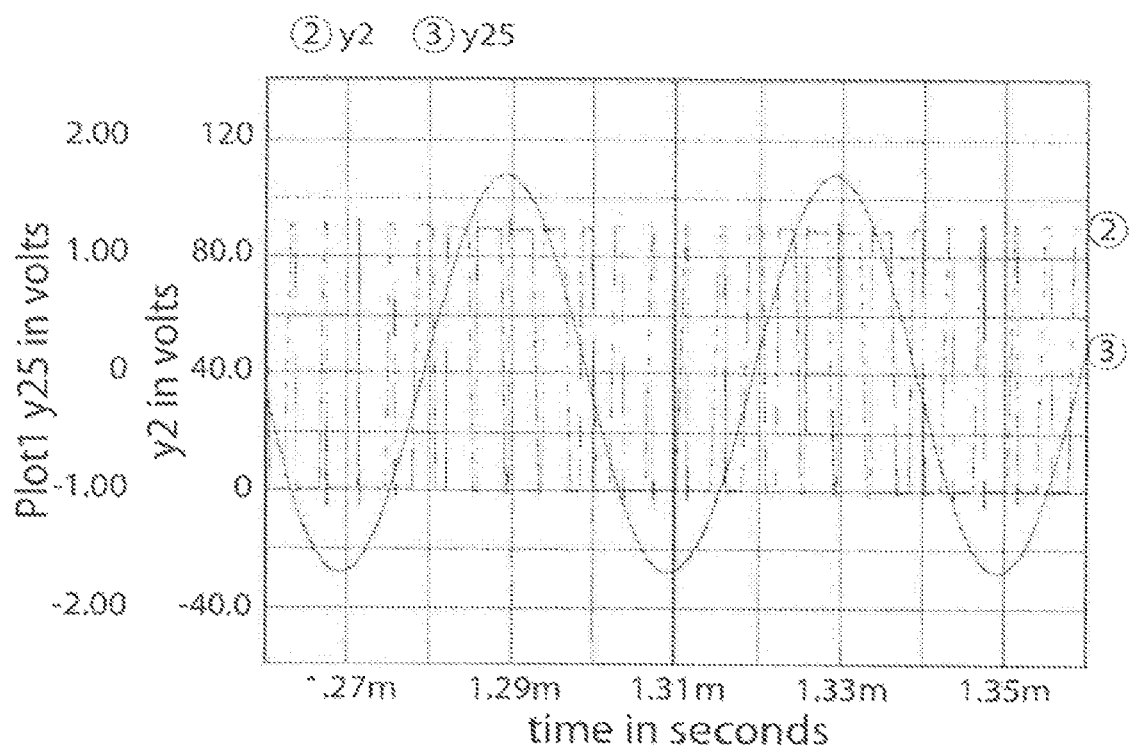

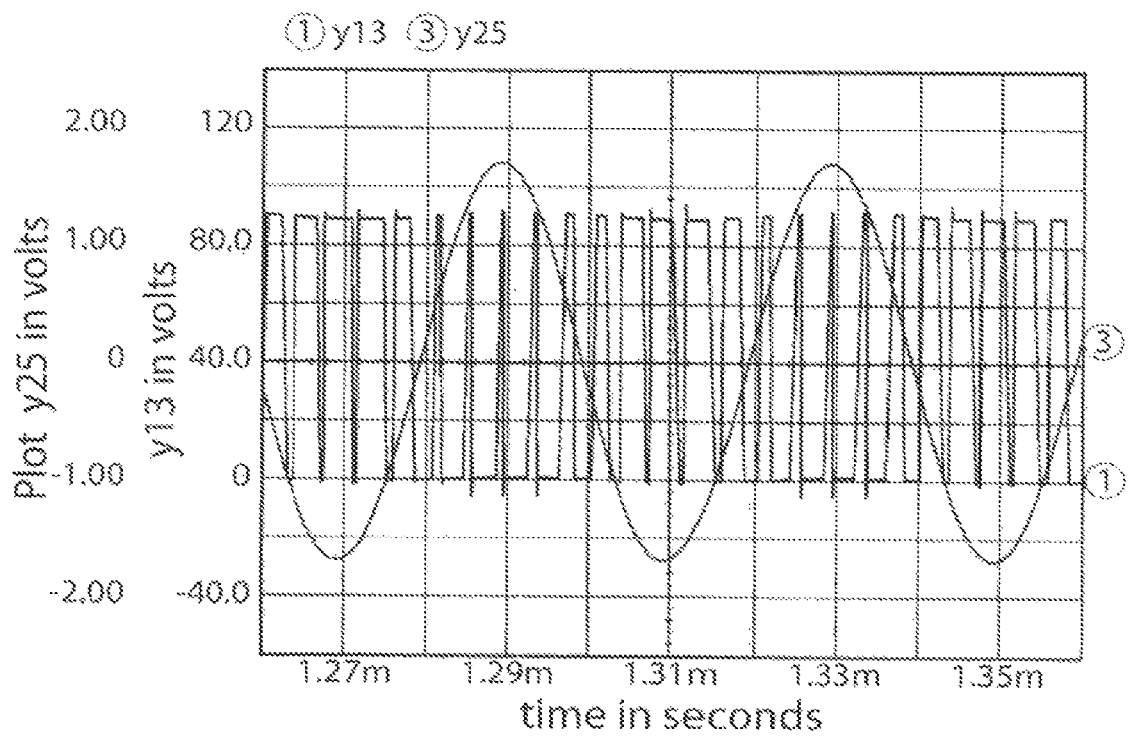

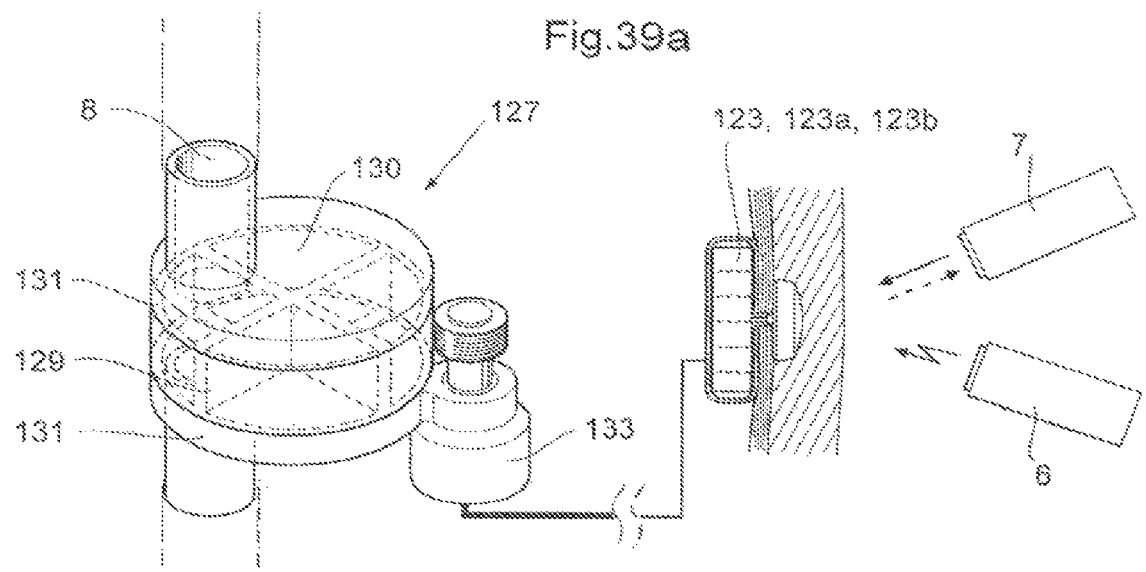
Fig.39a
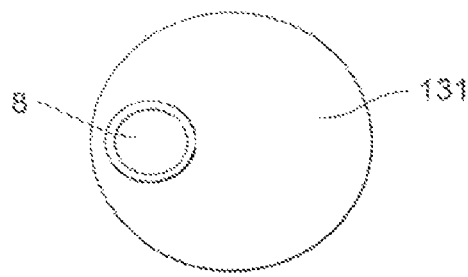
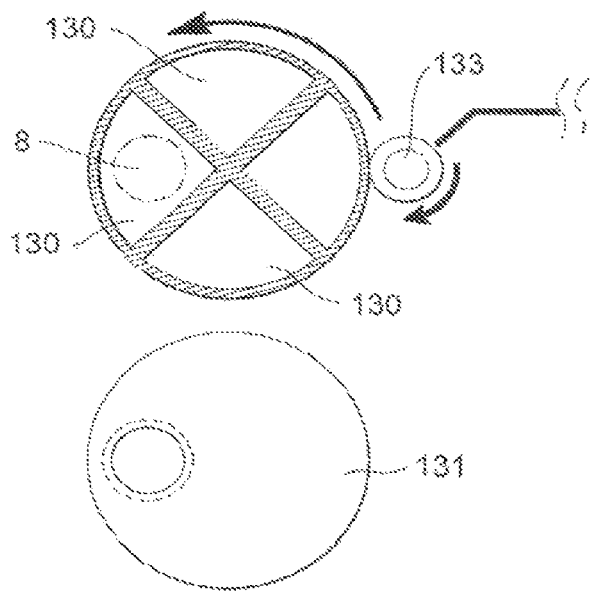
Fig.39b

DRAINAGE DEVICE COMPRISING A FILTER CLEANING DEVICE

This application is a continuation of U.S. application Ser. No. 15/730,768, filed Oct. 12, 2017, which Is continuation of U.S. application Ser. No. 12/864,695, filed Jan. 28, 2009, and Issued as U.S. Pat. No. 9,789,290 which is the U.S. national phase of International Application No. PCT/SE2009/000036, filed Jan. 28, 2009, which designated the U.S. and claims the benefit of U.S. Provisional Application No. 61/006,711, filed Jan. 28, 2008, the entire contents of each of which are hereby incorporated by reference in this application.

TECHNICAL FIELD

The present invention relates to a method and a device for draining body fluid.

BACKGROUND

Body fluid drains are used at so-called drainage sites for draining fluids from cavities in a patient's body, typically during and after surgical procedures. The drainage site may be a natural body cavity or orifice or may be surgically formed.

The drain device used for draining fluid from the body typically comprises a tube extending from the treatment area within the body through the skin of the patient and ending in a manual pump located outside the body. The pump is associated with a reservoir for storing the drained fluid. The reservoir is then emptied at suitable time intervals by manually compressing the reservoir.

A drain can be required for shorter or longer periods of time depending on the condition for which the drain is used. In particular when the drain is used for a longer period of time the drains existing today are cumbersome to use and impractical for the patient who is required to move the drain with him/her when moving around.

Also, U.S. Pat. No. 7,195,608 describes a drainage device for moving fluid to the urine bladder.

Hence, there exists a need for a drain that is less cumbersome to use and which enables a patient to more easily move around while still being attached to the drain.

SUMMARY

It is an object of the present invention to overcome or at least reduce some of the problems associated existing drainage devices It is another object of the present invention to provide a drainage device that enables a patient to more easily move around while still being attached to the drain.

It is yet another object to provide a drainage device that enables draining of fluids risking clogging the drainage device.

At least one of the above objects is obtained by the apparatus, device and method as set out in the appended claims. Thus, by providing an implantable drain adapted to move body fluid from one part of the body to another part of the body, a drainage device that which is completely implanted and which does not have any mechanical structure penetrating through the skin of the patient is obtained.

The apparatus for drainage of a body fluid in a human or mammal patient in accordance with the present invention comprises a drainage device for pumping body fluid. The drainage device is powered by an energy source and may be powered by any suitable means such as an electrical or a hydraulic motor. At least one connecting tube is connected to the drainage device so that the drainage device and the tube form a drainage arrangement. The drainage arrangement is adapted to be implanted inside the body of the patient, and placed so that the tube interconnects one part of the body with another part of the body and where drainage device is adapted to suck body fluid from the one part of the body via the tube to the other part of the body. Hereby an implantable drainage device is obtained which can pump body fluid from a treatment area to another part of the body where the fluid can be absorbed and transported out from the body in a normal way.

The implantable drainage device in accordance with the present invention can be used to move body fluid between different parts of the body depending on the type of body fluid being drained. For example and without limitation the drainage device can be adapted to drain urine from the urine accumulating renal part of the kidney, and moving the urine via at least one tube to the urine bladder. The drainage device can also be adapted to drain liquid from the hydrocephalus in the brain area, and moving it to the abdomen. The drainage device can also be adapted to drain liquid from ascites in the abdomen, and moving it to the lymphatic system of the body. Also, the drainage device can also be adapted to drain liquid from the thoraxial cavity, and moving the liquid to the abdomen.

Depending on the type of treatment and where the body fluid is sucked from and to where in the body the fluid is delivered the tubes used may be shaped to suit the particular treatment.

According to one embodiment there is provided a filter for removing clots and particles from the fluid passing through the drainage device. The filter can be powered by a suitable energy supply thereby providing an active filter. In accordance with one embodiment there is provided a powered cleaning device for cleaning the filter. One possibility is to clean the filter mechanically. In accordance with one embodiment the active filter is obtained by periodically changing the filter. The filter can be powered by any suitable energy source. In particular the same energy source used for the pump used for moving fluid through the drainage device can be used to power the active filter. By providing an active filter the filter can be cleaned a suitable times thereby reducing the risk that the filter will be clogged. The way of achieving a clean filter can either be by cleaning the filter while in place or by cleaning it while not in position. If the filter is cleaned while not in position in the fluid passageway of the drain, the drain can either be stopped while cleaning the filter or by replacing the filter with another filter.

In one embodiment a cassette of filter is provided. When a filter risks being clogged, the filter is replaced by another filter in the cassette. The used filter can then either be disposed of or be cleaned for later reuse.

In one embodiment the cassette is formed by a revolving cylinder comprising a number of filters. When the cylinder revolves on step a new filter is placed in the passageway of the drain.

The cleaning device preferably is adapted to move particles away from the passageway to a place free inside the patient's body, where the body itself will take care of the particles/clots.

Alternatively, a collecting volume, such as a bag, is provided for collecting particles that have been mechanically cleaned from the filter. Most likely such a bag will then be placed inside the body.

In one embodiment the filter is an active filer having moving parts. By driving the filter with an internal motor a cleaning device can be adapted to move particles away from the filter thereby cleaning it. Energy can be supplied to the filter in many ways. For example but without limitation the filter can be powered by wireless inductive energy or ultrasonic energy or light energy.

In one embodiment, the cleaning device is adapted to slice, push or scratch away any particles from the filter, but the cleaning device can also be adapted to suck away any particles from the filter.

In one embodiment, the cleaning device comprises a first piston, with preferably is provided with a first recess in an outer end portion thereof to collect particles and clots removed from the filter. By providing the first piston with a plurality of channels for accommodating the filter in an extended position of the first piston, it can surround the filter, ensuring essentially complete removal of particles therefrom. This is preferably performed if the first piston is movable in a direction perpendicular to the direction of the flow passageway.

The movement of the first piston can be controlled by a source of pressurized air, ensuring rapid acceleration of the first piston and thereby short cleaning cycles. The movement of the first piston can alternatively be controlled by an electric motor, a solenoid or the like.

The filter can in one embodiment be made of biocompatible material in order to avoid unnecessary interference with the environment.

In one embodiment, a second piston is provided across the flow passageway from the first piston, wherein the second piston is movable in a direction essentially perpendicular to the direction of the flow passageway and spring biased in the direction of the first piston. If an outer end portion of the second piston is provided with a second recess, the first piston and the second piston cooperate to catch particles for further removal. This further removal can be accomplished by means of a third piston, which is movable in a direction perpendicular to both the direction of the flow passageway and the direction of movement of the first piston and of the second piston.

In a preferred embodiment, the flow passageway of the cleaning device has an essentially square cross-sectional shape, which provides for a laminated flow, particularly if the square shape is combined with a filter comprising parallel strips.

The apparatus can comprise a switch, preferably a subcutaneous switch being adapted to manually and non-invasively control any function of the cleaning device.

The apparatus for removing particles preferably comprises a hydraulic device having a hydraulic reservoir, wherein the cleaning device is adapted to non-invasively be regulated by manually pressing the hydraulic reservoir.

A wireless remote control can non-invasively regulate any function of the cleaning device.

Even more important any function of the device may be programmable by such a remote control.

Also, a wireless energy transmitter can non-invasively energize the cleaning device. In one embodiment the same energy source is used for the pump of the drainage device and to power the cleaning device.

The apparatus preferably comprises a feedback device for sending information from inside the patient's body to the outside thereof to give feedback information related to at least one functional parameter of the device or a physical parameter of the patient, thereby optimizing the performance of the apparatus. One preferred functional parameter of the device is correlated to the transfer of energy for charging the internal energy source.

The apparatus preferably comprises an operation device for operating the cleaning device. This operation device can comprise a motor or a pump, an electrically powered operation device, a hydraulic operation device, or an electric motor.

To improve the performance of the apparatus for removing particles, a physical parameter sensor, such as a pressure sensor, is provided for sensing a physical parameter of the patient. An internal control unit can act in response to the physical parameter sensed by the sensor.

A functional parameter sensor sensing a functional parameter of the cleaning device can also be provided. An internal control unit acting in response to the functional parameter sensed by the sensor can also be provided.

A method of using the apparatus is also provided, wherein at least one function of the cleaning device is regulated from outside the patient's body. The regulation is in a preferred embodiment non-invasively by manually pressing a subcutaneous switch. In an alternative embodiment, non-invasively regulation is performed by manually pressing a hydraulic reservoir connected to the cleaning device.

Alternatively, the cleaning apparatus comprises a wireless remote control, wherein non-invasively regulation is performed using said remote control.

In a preferred embodiment, the cleaning apparatus for removing particles comprises a wireless energy transmitter, wherein non-invasively regulation is performed using said energy transmitter.

Preferably, an energy source is used for powering and adjusting any function of the cleaning device. The energy source may comprise an internal energy source, which preferably is associated with an external energy source adapted to transmit wireless energy. Energy is preferably transmitted from the external energy source to charge the internal energy source. Feedback information is preferably sent from inside the body to the outside thereof to give feedback related to the functional parameters of the device or physical parameters of the patient. The functional parameter of the device is correlated to the transfer of energy for charging the internal energy source.

In one embodiment, wireless energy is transmitted for powering the operation device.

In a preferred embodiment, the method of using a cleaning apparatus for removing particles comprises the steps of: implanting an implantable source of energy in the patient, providing an external source of energy, controlling the external source of energy to release wireless energy, charging non-invasively the implantable source of energy with the wireless energy, controlling the implantable source of energy from outside the patient's body, and releasing energy for use in connection with operation of the cleaning device. The wireless energy is preferably stored in the implantable source of energy.

In another preferred embodiment, the method of using an apparatus for removing particles comprises the steps of: providing an external source of energy outside the patient's body, and controlling the external source of energy from outside the patient's body to release wireless energy, and using released wireless energy for operating the operation device. The wireless energy is preferably transformed into electrical energy inside the patient's body using an implanted energy-transforming device and using the electrical energy when operating the cleaning device.

In one embodiment, the electrical energy is used directly in connection with operation of the cleaning device, as a transforming device transforms the wireless energy into the electrical energy.

In another embodiment, the external source of energy is controlled from outside the patient's body to release non-magnetic wireless energy, and released non-magnetic wireless energy is used for operating the cleaning device.

In yet an alternative embodiment, the external source of energy is controlled from outside the patient's body to release electromagnetic wireless energy, and released electromagnetic wireless energy is used for operating the cleaning device.

The invention also extends to a method for placing a cleaning device, comprising a surgical method via a laparoscopic abdominal approach. The method comprises the steps of: inserting a needle or tube like instrument into the abdomen of the patient's body, using the needle or tube like instrument to fill the patient's abdomen with gas thereby expanding the patient's abdominal cavity, placing at least two laparoscopic trocars in the patient's body, inserting a camera through one of the trocars into the patient's abdomen, inserting at least one dissecting tool through a trocar and dissecting the intended placement area of the patient, placing at least one cleaning device in any part of an implantable drainage device.

Further preferred embodiments are defined by the dependent claims.

BRIEF DESCRIPTION OF THE DRAWINGS

The present invention will now be described in more detail by way of non-limiting examples and with reference to the accompanying drawings, in which:

FIG. 7 is a sectional view similar to that of FIG. 4 showing particles before a cleaning operation.

FIG. 8 is a sectional view similar to that of FIG. 4 during a first step of a cleaning operation.

FIG. 9 is a sectional view similar to that of FIG. 4 during a second step of a cleaning operation.

FIG. 10 is a sectional view similar to that of FIG. 4 during a third step of a cleaning operation.

FIG. 14 is a schematic diagram of a cleaning apparatus.

FIGS. 15-30 show various embodiments based on the apparatus of FIG. 14.

FIG. 32 is a general view of an implanted drainage apparatus in a patient.

FIG. 33 is a detailed view of a drainage apparatus.

FIG. 36c-d are graphs showing different waveforms of signals in the amplifier of the ultrasonic embodiment.

FIGS. 39a and 39b are views of a filter cassette.

DETAILED DESCRIPTION

Figure 1A:
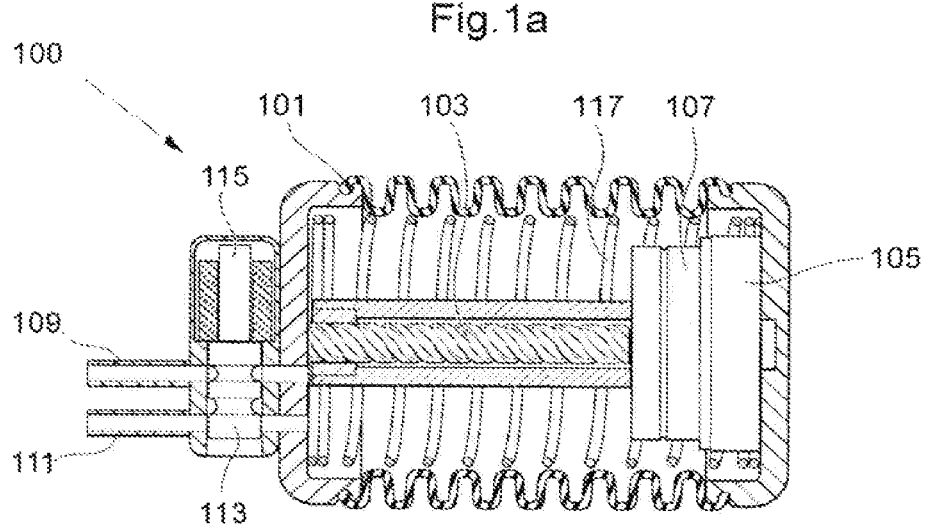
FIGS. 1a and 1b are views of an implantable drainage device in accordance with a first embodiment.
Figure 1B:
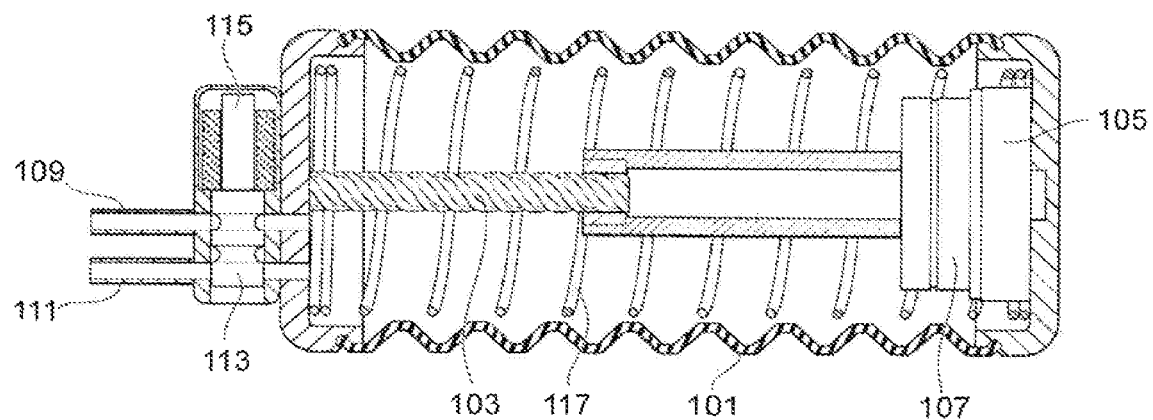

In FIGS. 1a and 1b a view illustrating an implantable drainage device 100. The device 100 comprises a bellow 101 adapted to move between a compressed position in which the bellow has a small inside volume and an expanded position in which the bellow has a larger inside volume. The view in FIG. 1a shows the bellow in a compressed position and the view in FIG. 1b shows the bellow in an expanded position.

The device 100 further comprises a member such as screw 103 adapted to compress the bellow 101. The screw 103 is accordance with one embodiment driven by a motor 105. The motor may many type of suitable motor including but not limited an electrical motor and a hydraulic motor. In accordance with one embodiment the motor is associated with a clutch 107 for regulating the power applied to the screw 103.

The inside of the bellow 101 is adapted receive and eject body fluid. The body fluid enters the bellow via an inlet 109 when the bellow expands. The fluid exits the bellow 101 via an outlet 111 when the bellow is compressed. In order for the fluid to only enter the bellow via the inlet when the bellow expands, a valve 113 is provided to prevent fluid to enter via the outlet 111 during the expansion phase. Similarly, the valve 113 is adapted to prevent fluid to exit via the inlet 109 when the bellow is compressed. The valve 113 is controlled by a control member 115 such as a solenoid.

The inlet and outlet are shaped to have tubes (not shown) fitted thereon. The tube connected to the inlet is preferably shaped and adapted to be placed in a treatment area from which body fluid is to be removed. The tube connected to the outlet is preferably shaped and adapted to be placed in a delivery area to which body fluid is to be moved from the treatment area.

During operation the device is adapted to compress the bellow in a compression phase during which fluid is ejected from the device 100 via the outlet tube to the delivery area for example by driving the motor to drive the screw. In a preferred embodiment a spring 117 is also compressed during the compression phase. During operation the device is further adapted to expand the bellow in an expansion phase during which fluid is sucked into the device 100 via the inlet tube from the treatment area for example by driving the screw in the opposite direction. In a preferred embodiment the spring 117 drives the bellow to expand during the expansion phase. When treating a patient the compression phase and expansion phase are continuously repeated whereby body fluid is removed from the treatment area to the delivery area.

Figure 2:
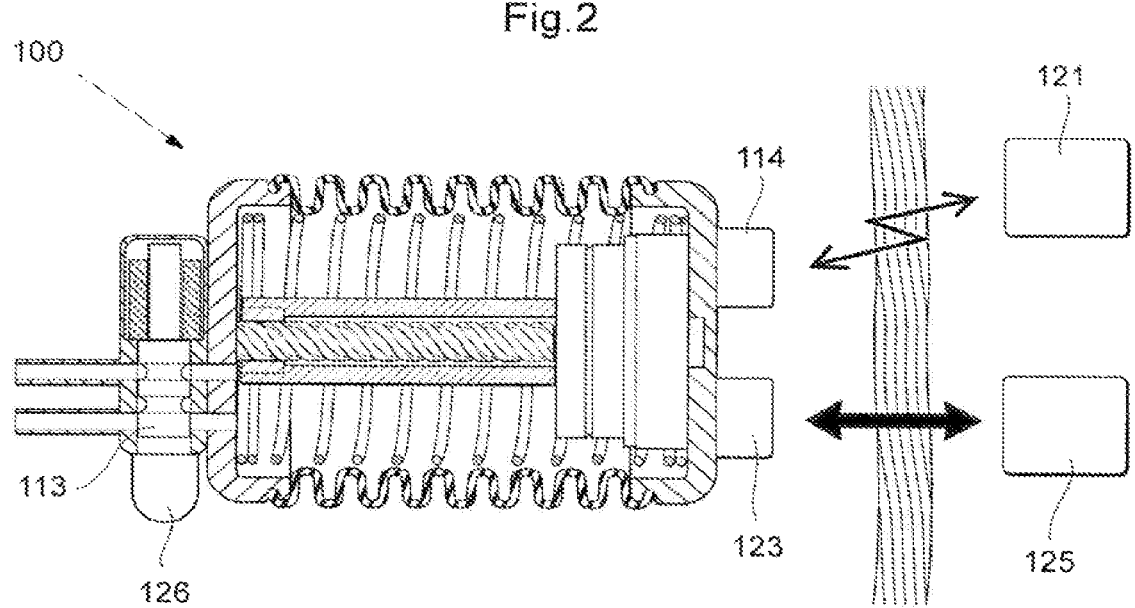
FIG. 2 is a view of an implantable drainage device in accordance with a second embodiment.

In FIG. 2 the device 100 is shown as supplemented with a control unit 119 for controlling the operation of the device 100. The control unit 119 can receive and transmit signals for a remote unit 121. The unit 121 is typically located outside the body when the device 100 is implanted inside a patient. In addition the device can be provided with a chargeable power source 123 connected to the motor. The power source 123 is adapted to receive wireless power from a second power source 125 which typically is located outside the patient when the implantable device 100 is implanted in a patient. Hereby the power source 123 can be recharged at suitable time intervals thereby removing the need for replacing the power source.

In order to prevent or remove a possible occlusion in the tube the drainage device can be provided with a backward release member 126 adapted to generate a backward pressure of fluid or air in the tube for removing or preventing a possible occlusion in the tube. The backward pressure is preferably repeatedly according to a predetermined time schedule. In accordance with one embodiment the release member comprises a pre-pressurized reservoir of air and a valve adapted to release a puff of air in the tube. In accordance with another embodiment the device 100 is adapted to move fluid or air in the tube in the reversed direction thereby creating a reverse flow for prevent or remove a possible occlusion in the tube. This can for example be obtained by controlling the valve 113 to a reversed more of operating so that fluid exits the device 100 via the inlet. In accordance with yet another embodiment a reservoir of the drainage is pre-pressurized by the pump, and a valve of the device is adapted to release a puff of fluid or air in the tube extending from the pre-pressurized reservoir when the pressure has reached a predetermined level.

source 123 connected to the motor. The power source 123 is adapted to receive wireless power from a second power source 125 which typically is located outside the patient when the implantable device 100 is implanted in a patient. Hereby the power source 123 can be recharged at suitable time intervals thereby removing the need for replacing the power source.

In order to prevent or remove a possible occlusion in the tube the drainage device can be provided with a backward release member 126 adapted to generate a backward pressure of fluid or air in the tube for removing or preventing a possible occlusion in the tube. The backward pressure is preferably repeatedly according to a predetermined time schedule. In accordance with one embodiment the release member comprises a pre-pressurized reservoir of air and a valve adapted to release a puff of air in the tube. In accordance with another embodiment the device 100 is adapted to move fluid or air in the tube in the reversed direction thereby creating a reverse flow for prevent or remove a possible occlusion in the tube. This can for example be obtained by controlling the valve 113 to a reversed more of operating so that fluid exits the device 100 via the inlet. In accordance with yet another embodiment a reservoir of the drainage is pre-pressurized by the pump, and a valve of the device is adapted to release a puff of fluid or air in the tube extending from the pre-pressurized reservoir when the pressure has reached a predetermined level.

Figure 3:
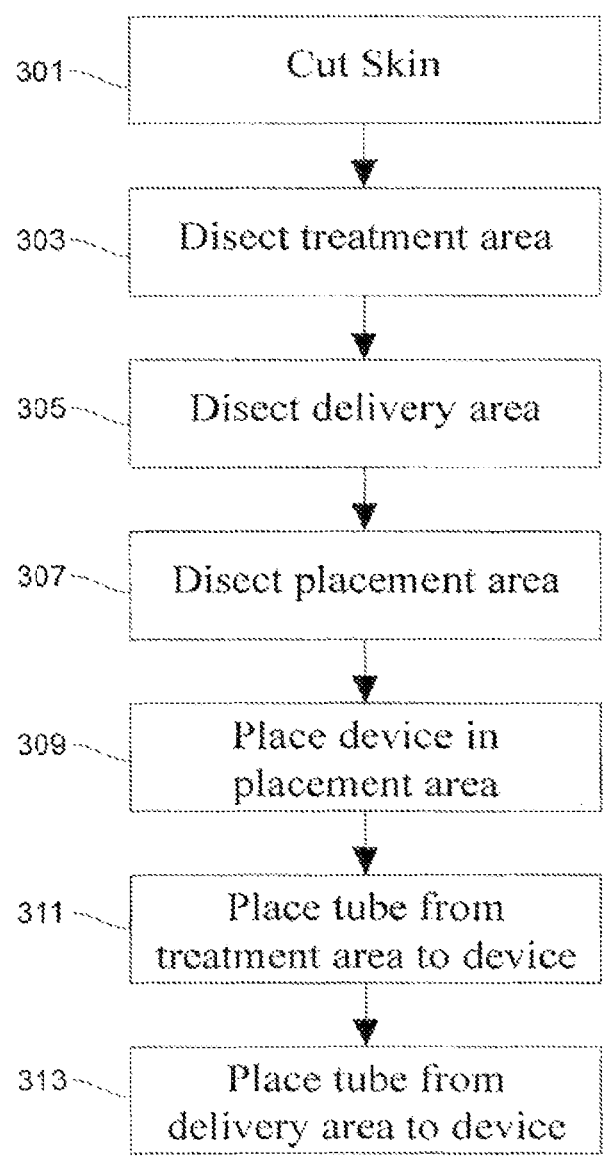
FIG. 3 is a flowchart illustrating different steps performed when implanting an implantable drainage device.
Figure 6:
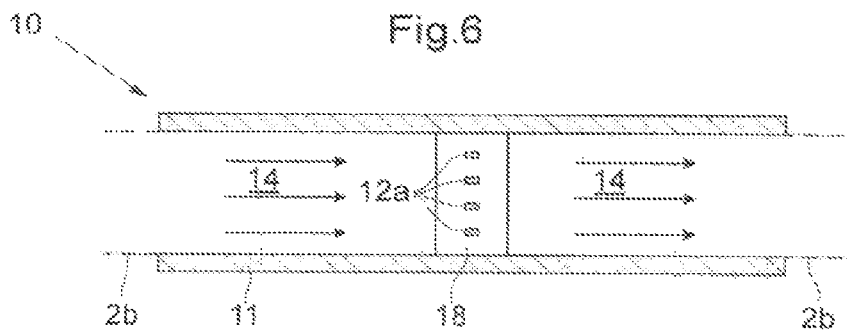
FIG. 6 is a sectional view of the cleaning device of FIG. 4 taken along the line IV-IV.

In FIG. 3 a flowchart illustrating step performed when implanting the device 100 in a patient. First in a step 301 the skin is cut at locations corresponding to the location where the device is to be placed and where the tubes leading to and from the device are going to be placed. Next, in a step 303 the area from which body fluid is to be removed, the treatment area is dissected. Then, in a step 305, the area to which body fluid is to be moved, the delivery area, is dissected. Thereupon, in a step 307, the area where the device is to be placed, the placement area is dissected, if the placement area is different from the treatment area and the delivery area. Next, in a step 309 the device is placed in the placement area and the By providing a plurality of strips 12a as a filter across the flow passageway 14, a laminar flow is achieved downstream of the filter, which is can be advantageous. The flow configuration can be further enhanced by giving the plurality of strips 12a a desired cross-sectional shape, although the rectangular shape shown in FIG. 6 will be adequate for most purposes.

A first piston 16 is provided movable in a direction essentially perpendicular to the direction of the flow passageway 14, i.e., essentially perpendicular to the direction of the flow. This first piston 16 is driven by some suitable actuator means, such as pressurized air, a solenoid arrangement, an electrical servo motor or the like. A motor could be used to build up a stored power that could be released very fast, one example being a spring. In a preferred embodiment, pressurized air acts as the actuator means, since by latching the piston by means of a suitable latching means for the piston, building up the air pressure, and subsequently releasing the piston, very high speed of the piston is achieved, with enables short cleaning times of the filter.

The outer end portion of the first piston 16, i.e., the end portion facing the flow passageway 14, is essentially flush with the wall of the flow passageway in a non-active state of the cleaning device 10. Also, the outer end portion is provided with a concave portion or recess 16a (exaggerated in the figures) in order to act as a particle capturing means, as will be explained below.

The strike range of the first piston 16 is preferably such that it extends all way across the flow passageway 14, as will be explained below with reference to FIGS. 7-10. A number of channels 16b corresponding to the number of strips 12a is provided in the first piston 16 to accommodate the strips when the first piston is in an extended position.

The first piston 16 is also provided with a plurality of through holes 17 in the direction of the flow passageway. These through holes will allow a flow through the flow passageway also during a cleaning operation, as will be explained below with reference to FIG. 11.

A second piston 18 is provided across the flow passageway 14 from the first piston 16. Also this second piston 18 is movable in a direction essentially perpendicular to the direction of the flow passageway 14 and is biased in the direction thereof by means of a spring 18a, for example. Likewise, the outer end portion of the second piston is provided with a recess 18b similar to the recess 16a of the first piston 16.

The first and second pistons 16, 18, are sealed to the housing 11 by means of a respective sealing 20, such as an O sealing.

Figure 4:
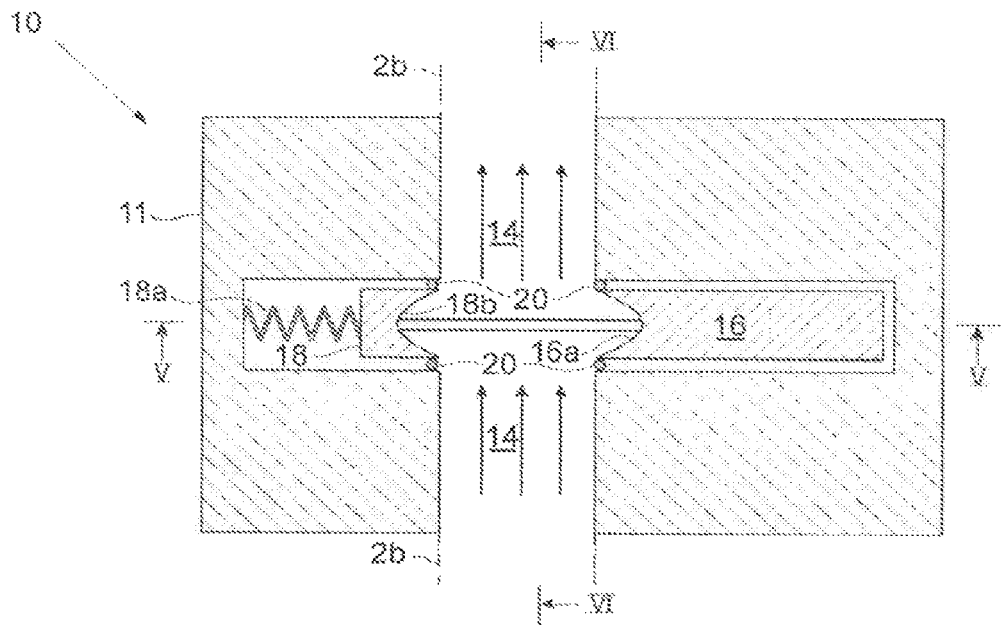
FIG. 4 is a sectional view of a cleaning device according to the invention.
Figure 5:
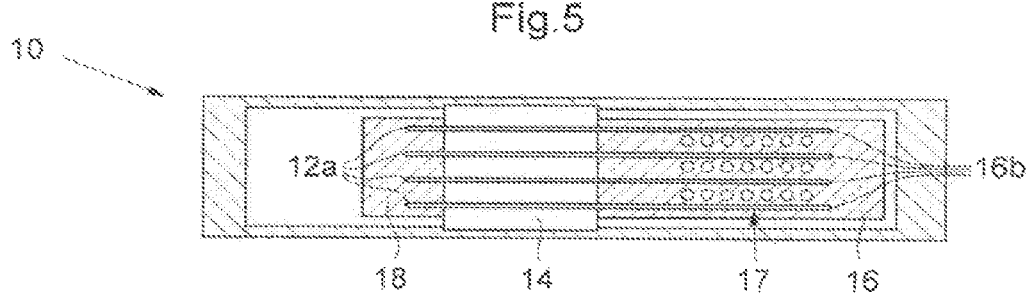
FIG. 5 is a cross sectional view of the cleaning device of FIG. 4 taken along the line III-III before a cleaning operation.

A preferred embodiment of a cleaning method according to the invention will now be described with reference to FIGS. 7-10, showing different operational steps of the above-described device. FIG. 7 is a view similar to that of FIG. 4. However, this figure shows the cleaning device 10 during operation, wherein particles, generally designated 22, have assembled on the filter 12.

In FIG. 8, the first piston 16 has moved linearly from the retracted starting position shown FIG. 7 to an extended position, wherein the outer end portion thereof is in contact with the second piston 18. Due to the recess 16*a* in the outer end of the first piston 16, the particles 22 have been assembled in the recess 16*a*, whereby they have been brought with the first piston 16 during the movement thereof. In the step shown in FIG. 8, the particles are confined in the recess 16*a* between the first and second pistons 16, 18.

By moving the first piston 16 an additional distance from the position shown in FIG. 8, the second piston 18 is pushed against the force of the spring 18*a* to a fully retracted position, see FIG. 9. The plurality of strips 12*a* is in this position fully received in a respective channel 16*b* in the first piston. It is seen that the outer ends of the first and second pistons define an unobstructed cavity in which the particles are confined. It is thereby possible to remove these by some suitable means. One such means could be a third piston 24, which is movable in a direction perpendicular to both the direction of the flow passageway 14 and the direction of movement of the first and second pistons 16, 18. This third piston, the movement of which could be controlled by means of pressurized air, a solenoid, an electric motor etc., scrapes off the particles collected by the first piston 16 and moves them to a place outside of the cleaning device 10 and the flow passageway 14.

Figure 11:
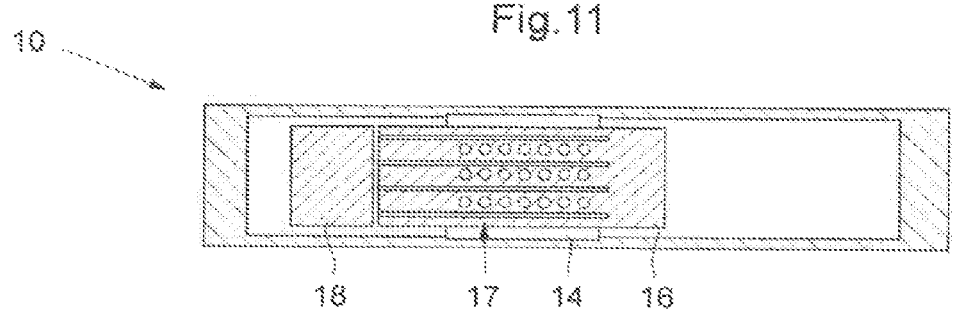
FIG. 11 is a cross sectional view similar to that of FIG. 5 during a cleaning operation.

FIG. 11 shows a side view of the first piston 16 in a fully extended position, i.e., corresponding to the view of FIG. 10. It is here seen that in this position the through holes 17 will be aligned with the flow passageway 14, thereby allowing a flow therethrough also during cleaning of the filter 12.

Figure 12:
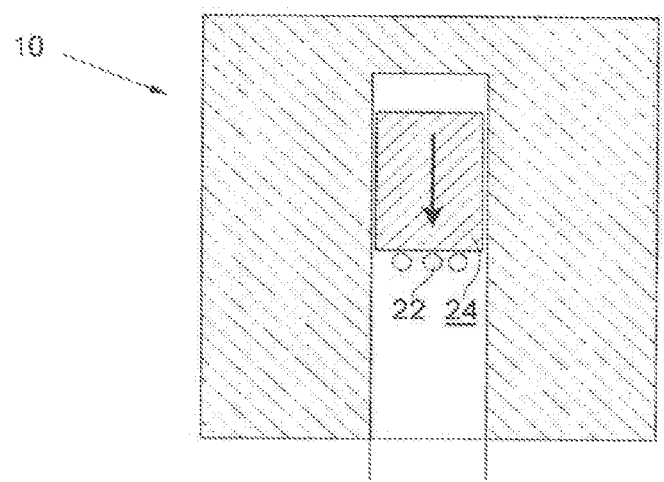
FIG. 12 is a sectional view of the cleaning device of FIG. 10 taken along the line X-X showing a cleaning ejection piston before ejection of particles.
Figure 13:
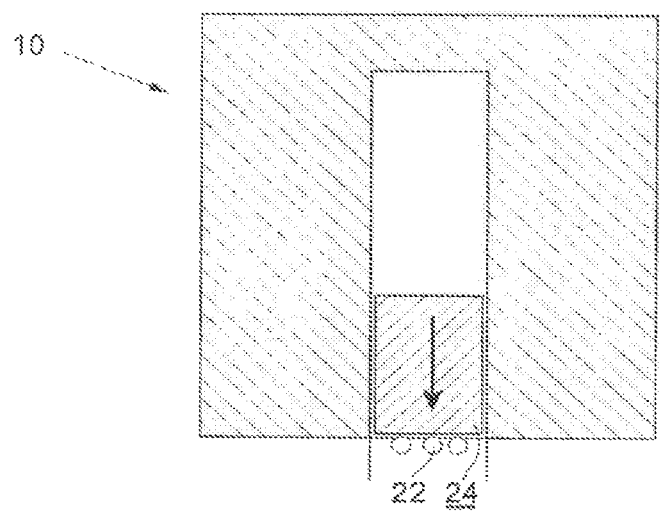
FIG. 13 is a view similar to that of FIG. 11 but after ejection of particles.

FIG. 12 shows a cross-sectional view taken along line X-X of FIG. 10. It is here seen that the third piston 24 collects the particles 22 during a downward movement, indicated by an arrow in the figure. The particles are ejected from the cleaning device 10 when the third piston 24 has reached its lower end position, shown in FIG. 13.

Again with reference to FIG. 9, it will be realized that pressurized air can be used for ejecting the collected particles from the cavity formed by the first piston 16 and the second piston 18.

A cleaning apparatus, generally designated 28 and comprising a cleaning device as described above will now be described with reference to FIGS. 14-26.

A cleaning apparatus is shown in a more generalized block diagram form in FIG. 14, wherein the patient's skin 36, generally shown by a vertical line, separates the interior of the patient to the right of the line from the exterior to the left of the line.

FIG. 15 shows an embodiment of the invention identical to that of FIG. 14, except that a reversing device in the form of an electric switch 38 operable by polarized energy also is implanted in the patient for reversing the cleaning device 10. The wireless remote control of the external energy transmission device 34 transmits a wireless signal that carries polarized energy and the implanted energy transforming device 30 transforms the wireless polarized energy into a polarized current for operating the electric switch 38. When the polarity of the current is shifted by the implanted energy transforming device 30 the electric switch 38 reverses the function performed by the cleaning device 10.

FIG. 16 shows an embodiment of the invention identical to that of FIG. 14, except that an operation device 40 implanted in the patient for regulating the cleaning device 10 is provided between the implanted energy transforming device 30 and the cleaning device 10. This operation device can be in the form of a motor 40, such as an electric servo motor. The motor 40 is powered with energy from the implanted energy transforming device 30, as the remote control of the external energy transmission device 34 transmits a wireless signal to the receiver of the implanted energy transforming device 30.

FIG. 17 shows an embodiment of the invention identical to that of FIG. 14, except that it also comprises an operation device is in the form of an assembly 42 including a motor/pump unit 78 and a fluid reservoir 46 is implanted in the patient. In this case the cleaning device 10 is hydraulically operated, i.e. hydraulic fluid is pumped by the motor/pump unit 44 from the fluid reservoir 46 through a conduit 48 to the cleaning device 10 to operate the cleaning device, and hydraulic fluid is pumped by the motor/pump unit 44 back from the cleaning device 10 to the fluid reservoir 46 to return the cleaning device to a starting position. The implanted energy transforming device 30 transforms wireless energy into a current, for example a polarized current, for powering the motor/pump unit 44 via an electric power supply line 50.

Instead of a hydraulically operated cleaning device 10, it is also envisaged that the operation device comprises a pneumatic operation device. In this case, pressurized air can be used for regulation and the fluid reservoir is replaced by an air chamber and the fluid is replaced by air.

Figure 18:
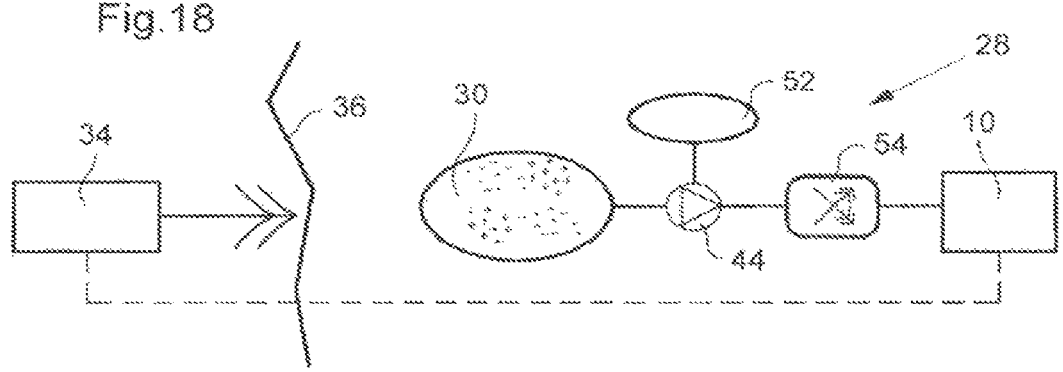

FIG. 18 shows an embodiment of the invention comprising the external energy transmission device 34 with its wireless remote control, the cleaning device 10, in this case hydraulically operated, and the implanted energy transforming device 30, and further comprising a hydraulic fluid reservoir 52, a motor/pump unit 44 and an reversing device in the form of a hydraulic valve shifting device 54, all implanted in the patient. The motor of the motor/pump unit 44 is an electric motor. In response to a control signal from the wireless remote control of the external energy transmission device 34, the implanted energy transforming device 30 powers the motor/pump unit 44 with energy from the energy carried by the control signal, whereby the motor/pump unit 44 distributes hydraulic fluid between the hydraulic fluid reservoir 52 and the cleaning device 10. The remote control of the external energy transmission device 34 controls the hydraulic valve shifting device 54 to shift the hydraulic fluid flow direction between one direction in which the fluid is pumped by the motor/pump unit 44 from the hydraulic fluid reservoir 52 to the cleaning device 10 to operate the cleaning device, and another opposite direction in which the fluid is pumped by the motor/pump unit 44 back from the cleaning device 10 to the hydraulic fluid reservoir 52 to return the cleaning device to a starting position.

Figure 19:
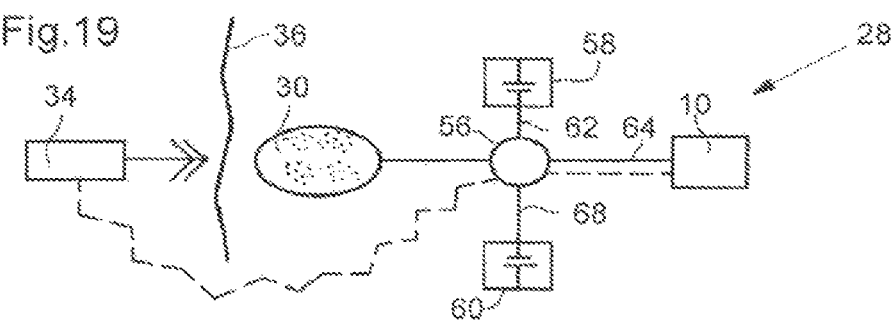

FIG. 19 shows an embodiment of the invention identical to that of FIG. 14, except that an internal control unit 56 controlled by the wireless remote control of the external energy transmission device 34, an accumulator 58 and a capacitor 60 also are implanted in the patient. The internal control unit 56 arranges storage of electric energy received from the implanted energy transforming device 30 in the accumulator 58, which supplies energy to the cleaning device 10. In response to a control signal from the wireless remote control of the external energy transmission device 34, the internal control unit 56 either releases electric energy from the accumulator 58 and transforms the released energy via power lines 62 and 64, or directly transforms electric energy from the implanted energy transforming device 30 via a power line 66, the capacitor 60, which stabilizes the electric current, a power line 68 and the power line 64, for the operation of the cleaning device 10.

The internal control unit is preferably programmable from outside the patient's body. In a preferred embodiment, the internal control unit is programmed to regulate the cleaning device 10 to remove any particles from the drainage device and place the particles outside the drainage device repeatedly according to a pre-programmed time-schedule.

In accordance with an alternative, the capacitor 60 in the embodiment of FIG. 19 may be omitted. In accordance with another alternative, the accumulator 58 in this embodiment may be omitted.

Figure 20:
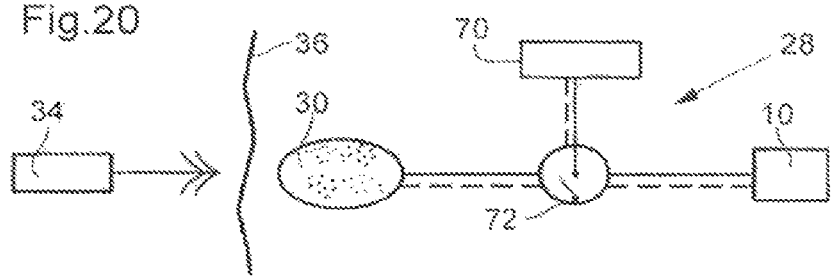

FIG. 20 shows an embodiment of the invention identical to that of FIG. 14, except that a battery 70 for supplying energy for the operation of the cleaning device 10 and an electric switch 72 for switching the operation of the cleaning device 10 also are implanted in the patient. The electric switch 72 is operated by the energy supplied by the implanted energy transforming device 30 to switch from an off mode, in which the battery 70 is not in use, to an on mode, in which the battery 70 supplies energy for the operation of the cleaning device 10.

Figure 21:
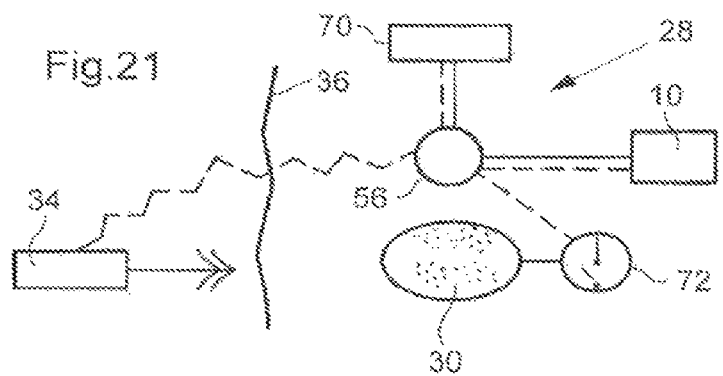

FIG. 21 shows an embodiment of the invention identical to that of FIG. 20, except that an internal control unit 56 controllable by the wireless remote control of the external energy transmission device 34 also is implanted in the patient. In this case, the electric switch 72 is operated by the energy supplied by the implanted energy transforming device 30 to switch from an off mode, in which the wireless remote control is prevented from controlling the internal control unit 56 and the battery is not in use, to a standby mode, in which the remote control is permitted to control the internal control unit 56 to release electric energy from the battery 70 for the operation of the cleaning device 10.

Figure 22:
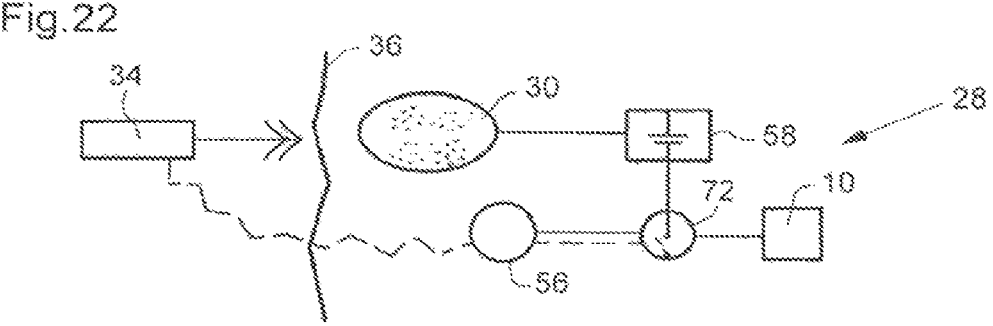

FIG. 22 shows an embodiment of the invention identical to that of FIG. 21, except that an accumulator 58 is substituted for the battery 70 and the implanted components are interconnected differently. In this case, the accumulator 58 stores energy from the implanted energy transforming device 30. In response to a control signal from the wireless remote control of the external energy transmission device 34, the internal control unit 56 controls the electric switch 72 to switch from an off mode, in which the accumulator 58 is not in use, to an on mode, in which the accumulator 58 supplies energy for the operation of the cleaning device 10.

Figure 23:
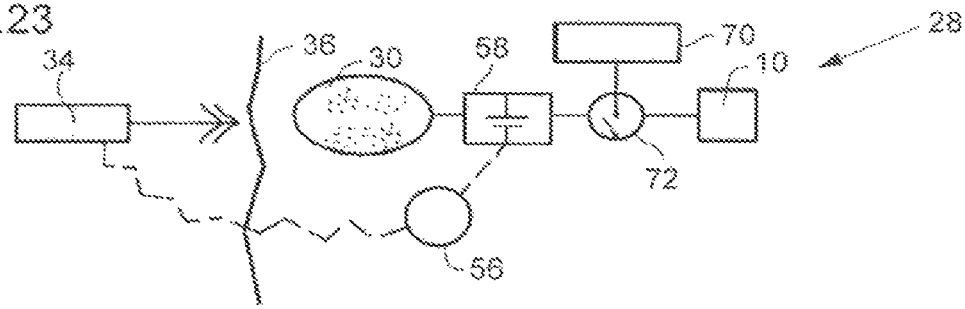

FIG. 23 shows an embodiment of the invention identical to that of FIG. 22, except that a battery 70 also is implanted in the patient and the implanted components are interconnected differently. In response to a control signal from the wireless remote control of the external energy transmission device 34, the internal control unit 56 controls the accumulator 58 to deliver energy for operating the electric switch 72 to switch from an off mode, in which the battery 70 is not in use, to an on mode, in which the battery 70 supplies electric energy for the operation of the cleaning device 10.

Alternatively, the electric switch 72 may be operated by energy supplied by the accumulator 58 to switch from an off mode, in which the wireless remote control is prevented from controlling the battery 70 to supply electric energy and is not in use, to a standby mode, in which the wireless remote control is permitted to control the battery 70 to supply electric energy for the operation of the cleaning device 10.

Figure 24:
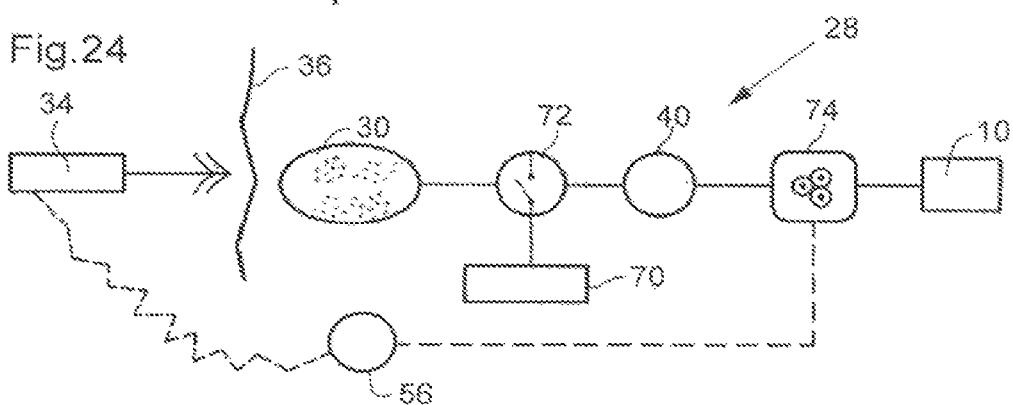

FIG. 24 shows an embodiment of the invention identical to that of FIG. 20, except that a motor 40, a mechanical reversing device in the form of a gear box 74, and an internal control unit 56 for controlling the gear box 74 also are implanted in the patient. The internal control unit 56 controls the gear box 74 to reverse the function performed by the cleaning device 10 (mechanically operated).

Figure 25:
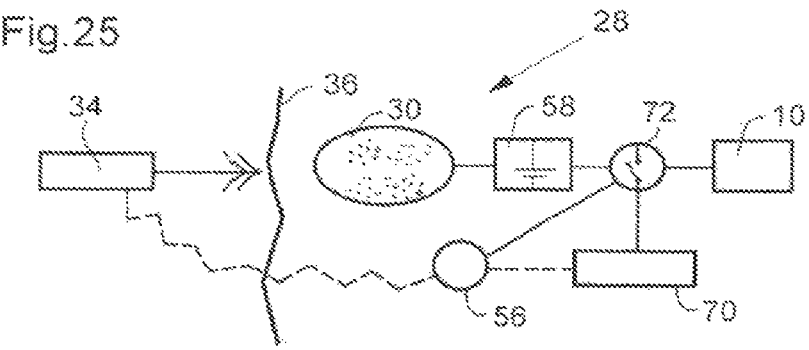

FIG. 25 shows an embodiment of the invention identical to that of FIG. 23 except that the implanted components are interconnected differently. Thus, in this case the internal control unit 56 is powered by the battery 70 when the accumulator 58, suitably a capacitor, activates the electric switch 72 to switch to an on mode. When the electric switch 72 is in its on mode the internal control unit 56 is permitted to control the battery 70 to supply, or not supply, energy for the operation of the cleaning device 10.

Figure 26:
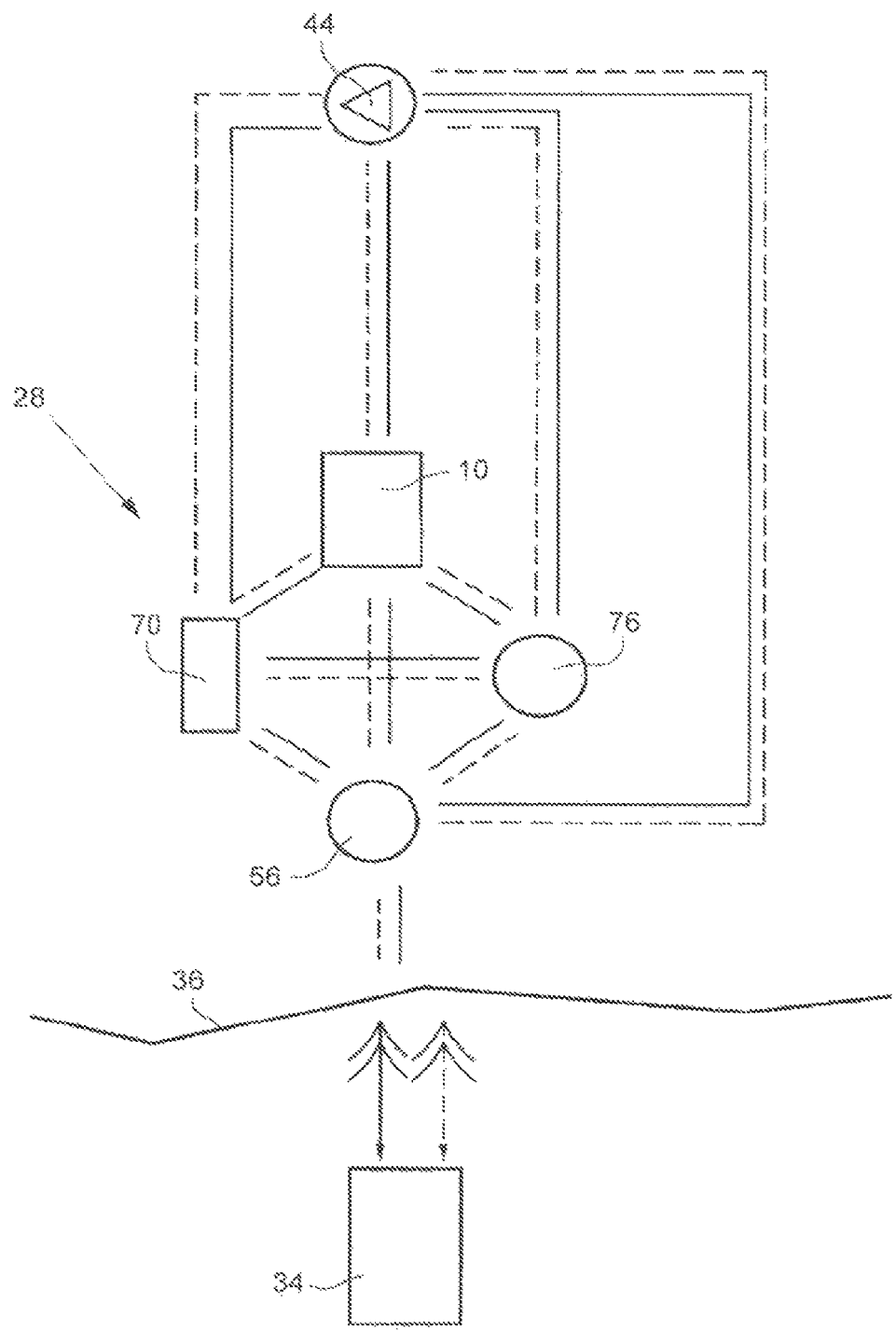

FIG. 26 schematically shows conceivable combinations of implanted components of the apparatus for achieving various communication options. Basically, there are the cleaning device 10, the internal control unit 56, motor/pump unit 44, and the external energy transmission device 34 including the external wireless remote control. As already described above the wireless remote control transmits a control signal which is received by the internal control unit 56, which in turn controls the various implanted components of the apparatus.

A feedback device, preferably in the form of a sensor 76, may be implanted in the patient for sensing a physical parameter of the patient, such as the pressure in a blood vessel. The internal control unit 56, or alternatively the external wireless remote control of the external energy transmission device 34, may control the cleaning device 10 in response to signals from the sensor 76. A transceiver may be combined with the sensor 76 for sending information on the sensed physical parameter to the external wireless remote control. The wireless remote control may comprise a signal transmitter or transceiver and the internal control unit 56 may comprise a signal receiver or transceiver. Alternatively, the wireless remote control may comprise a signal receiver or transceiver and the internal control unit 56 may comprise a signal transmitter or transceiver. The above transceivers, transmitters and receivers may be used for sending information or data related to the cleaning device 10 from inside the patient's body to the outside thereof.

Alternatively, the sensor 76 may be arranged to sense a functional parameter of the cleaning device 10.

Where the motor/pump unit 44 and battery 70 for powering the motor/pump unit 44 are implanted, the battery 70 may be equipped with a transceiver for sending information on the condition of the battery 70.

Figure 27:
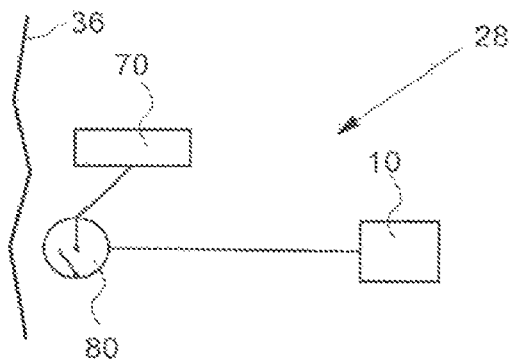

FIG. 27 shows an alternative embodiment wherein the cleaning device 10 is regulated from outside the patient's body. The cleaning apparatus 28 comprises a cleaning device 10 connected to a battery 70 via a subcutaneous switch 80. Thus, the regulation of the cleaning device 10 is performed non-invasively by manually pressing the subcutaneous switch, whereby the operation of the cleaning device 10 is switched on and off. It will be appreciated that the shown embodiment is a simplification and that additional components, such as an internal control unit, can be added to the cleaning apparatus.

Figure 28:
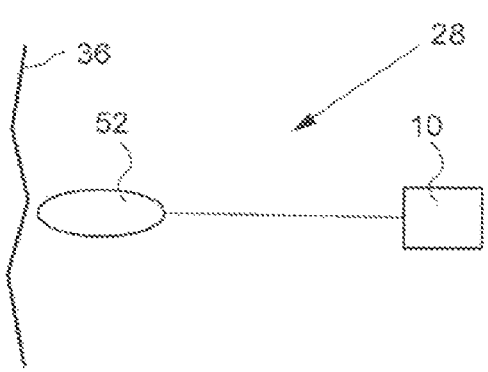

FIG. 28 shows an alternative embodiment, wherein the cleaning apparatus 28 comprises a cleaning device 10 in fluid connection with a hydraulic fluid reservoir 52. Non-invasive regulation is performed by manually pressing the hydraulic reservoir connected to the cleaning device 10.

A further embodiment of a apparatus according to the invention comprises a feedback device for sending information from inside the patient's body to the outside thereof to give feedback information related to at least one functional parameter of the clot removal device or apparatus or a physical parameter of the patient, thereby optimizing the performance of the apparatus.

One preferred functional parameter of the device is correlated to the transfer of energy for charging the internal energy source.

Figure 29:
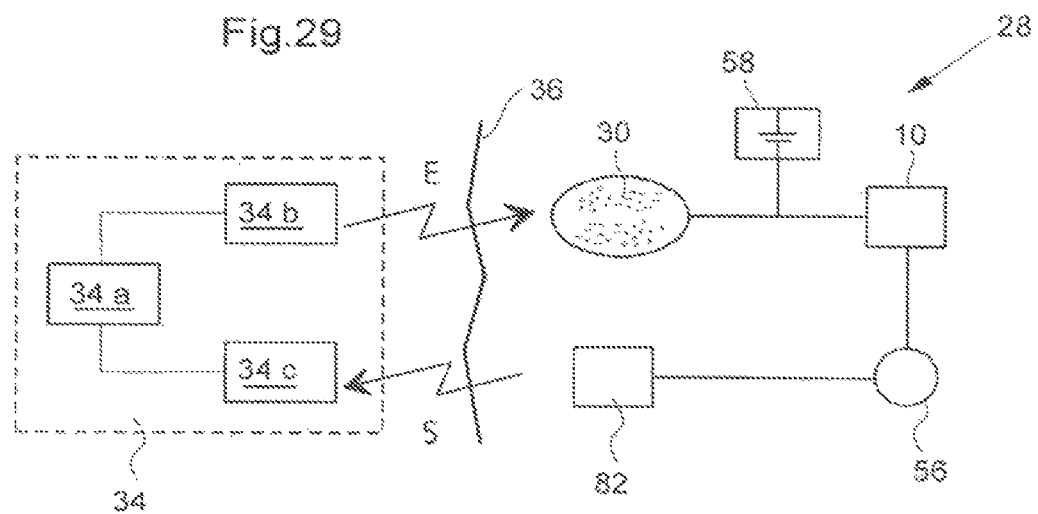

In FIG. 29, an arrangement is schematically illustrated for supplying an accurate amount of energy to a cleaning apparatus 28 implanted in a patient, whose skin 36 is indicated by a vertical line. A cleaning device 10 is connected to an implanted energy transforming device 30, likewise located inside the patient, preferably just beneath the patient's skin 36. Generally speaking, the implanted energy transforming device 30 may be placed in the abdomen, thorax, muscle fascia (e.g. in the abdominal wall), subcutaneously, or at any other suitable location. The implanted energy transforming device 30 is adapted to receive wireless energy E transmitted from an external energy source 34a provided in the external energy transmission device 34 located outside the patient's skin 36 in the vicinity of the implanted energy transforming device 30.

As is well known in the art, the wireless energy E may generally be transferred by means of any suitable Transcutaneous Energy Transfer (TET) device, such as a device including a primary coil arranged in the external energy source 34a and an adjacent secondary coil arranged in the implanted energy transforming device 30. When an electric current is fed through the primary coil, energy in the form of a voltage is induced in the secondary coil which can be used to operate a cleaning device, e.g. after storing the incoming energy in an energy storing device or accumulator, such as a battery or a capacitor. However, the present invention is generally not limited to any particular energy transfer technique, TET devices or energy storing devices, and any kind of wireless energy may be used. Other energy transfer methods include but are not limited to non-induction methods such as by means of ultra-sonic devices or using light.

The amount of transferred energy can be regulated by means of an external control unit 34b controlling the external energy source 34a based on the determined energy balance, as described above. In order to transfer the correct amount of energy, the energy balance and the required amount of energy can be determined by means of an internal control unit 56 connected to the cleaning device 10. The internal control unit 56 may thus be arranged to receive various measurements obtained by suitable sensors or the like, not shown, measuring certain characteristics of the cleaning device 10, reflecting the required amount of energy needed for proper operation of the cleaning device 10. Moreover, the current condition of the patient may also be detected by means of suitable measuring devices or sensors, in order to provide parameters reflecting the patient's condition. Hence, such characteristics and/or parameters may be related to the current state of the cleaning device 10, such as power consumption, operational mode and temperature, as well as the patient's condition reflected by, e.g., body temperature, blood pressure, heartbeats and breathing.

Furthermore, an energy storing device or accumulator 58 may optionally be connected to the implanted energy transforming device 30 for accumulating received energy for later use by the cleaning device 10. Alternatively or additionally, characteristics of such an accumulator, also reflecting the required amount of energy, may be measured as well. The accumulator may be replaced by a battery, and the measured characteristics may be related to the current state of the battery, such as voltage, temperature, etc. In order to provide sufficient voltage and current to the cleaning device 10, and also to avoid excessive heating, it is clearly understood that the battery should be charged optimally by receiving a correct amount of energy from the implanted energy transforming device 30, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 56. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 56 is adapted to determine the energy balance and/or the currently required amount of energy, (either energy per time unit or accumulated energy) based on measurements made by the above-mentioned sensors or measuring devices on the cleaning device 10, or the patient, or an energy storing device if used, or any combination thereof. The internal control unit 56 is further connected to an internal signal transmitter 82, arranged to transmit a control signal reflecting the determined required amount of energy, to an external signal receiver 34c connected to the external control unit 34b. The amount of energy transmitted from the external energy source 34a may then be regulated in response to the received control signal.

Alternatively, sensor measurements can be transmitted directly to the external control unit 34b wherein the energy balance and/or the currently required amount of energy can be determined by the external control unit 34b, thus integrating the above-described function of the internal control unit 56 in the external control unit 34b. In that case, the internal control unit 56 can be omitted and the sensor measurements are supplied directly to the internal signal transmitter 82 which sends the measurements over to the external signal receiver 34c and the external control unit 34b. The energy balance and the currently required amount of energy can then be determined by the external control unit 34b based on those sensor measurements.

Hence, feedback of information indicating the required energy can be used, which is more efficient because it is based on the actual use of energy that is compared to for example the received energy, e.g. with respect to the amount of energy, the energy difference, or the energy receiving rate as compared to the energy rate used by the cleaning device. The cleaning device may use the received energy either for consuming or for storing the energy in an energy storage device or the like. The different parameters discussed above would thus be used if relevant and needed and then as a tool for determining the actual energy balance. However, such parameters may also be needed per se for any actions taken internally to specifically operate the clot removal device.

The internal signal transmitter 82 and the external signal receiver 34c may be implemented as separate units using suitable signal transfer means, such as radio, IR (Infrared) or ultrasonic signals. Alternatively, the internal signal transmitter 82 and the external signal receiver 34c may be integrated in the implanted energy transforming device 30 and the external energy source 34a, respectively, so as to convey control signals in a reverse direction relative to the energy transfer, basically using the same transmission technique. The control signals may be modulated with respect to frequency, phase or amplitude.

The energy supply arrangement illustrated in FIG. 29 may operate basically in the following manner. The energy balance is first determined by the internal control unit 56. A control signal reflecting the required amount of energy is also created by the internal control unit 56, and the control signal is transmitted from the internal signal transmitter 82 to the external signal receiver 34c. Alternatively, the energy balance can be determined by the external control unit 34b instead depending on the implementation, as mentioned above. In that case, the control signal may carry measurement results from various sensors. The amount of energy emitted from the external energy source 34a can then be regulated by the external control unit 34b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 34a, such as voltage, current, amplitude, wave frequency and pulse characteristics.

A method is thus provided for controlling transmission of wireless energy supplied to an electrically operable cleaning device implanted in a patient. The wireless energy E is transmitted from an external energy source located outside the patient and is received by an internal energy receiver located inside the patient, the internal energy receiver being connected to the clot removal device for directly or indirectly supplying received energy thereto. An energy balance is determined between the energy received by the internal energy receiver and the energy used for the cleaning device. The transmission of wireless energy E from the external energy source is then controlled based on the determined energy balance.

A apparatus is also provided for controlling transmission of wireless energy supplied to an electrically operable cleaning device implanted in a patient. The apparatus is adapted to transmit the wireless energy E from an external energy source located outside the patient which is received by an implanted energy transforming device located inside the patient, the implanted energy transforming device being connected to the cleaning device for directly or indirectly supplying received energy thereto. The apparatus is further adapted to determine an energy balance between the energy received by the implanted energy transforming device and the energy used for the cleaning device, and control the transmission of wireless energy E from the external energy source, based on the determined energy balance.

The functional parameter of the device is correlated to the transfer of energy for charging the internal energy source.

In yet an alternative embodiment, the external source of energy is controlled from outside the patient's body to release electromagnetic wireless energy, and released electromagnetic wireless energy is used for operating the cleaning device.

In another embodiment, the external source of energy is controlling from outside the patient's body to release non-magnetic wireless energy, and released non-magnetic wireless energy is used for operating the cleaning device.

Those skilled in the art will realize that the above various embodiments according to FIGS. 14-30 could be combined in many different ways. For example, the electric switch 38 operated polarized energy could be incorporated in any of the embodiments of FIGS. 16, 19-25, the hydraulic valve shifting device 54 could be incorporated in the embodiment of FIG. 17, and the gear box 74 could be incorporated in the embodiment of FIG. 16.

Figure 30:
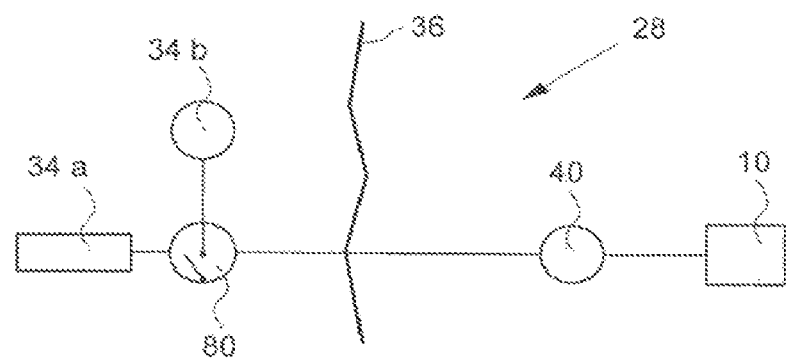

Wireless transfer of energy for operating the cleaning device has been described to enable non-invasive operation. It will be appreciated that the cleaning device can be operated with wire bound energy as well. One such example is shown in FIG. 30, wherein an external switch 84 is interconnected between the external energy source 34a and an operation device, such as an electric motor regulating the cleaning device 10, by means of power lines 86 and 88. An external control unit 34b controls the operation of the external switch to effect proper operation of the cleaning device 10.

Figure 31:
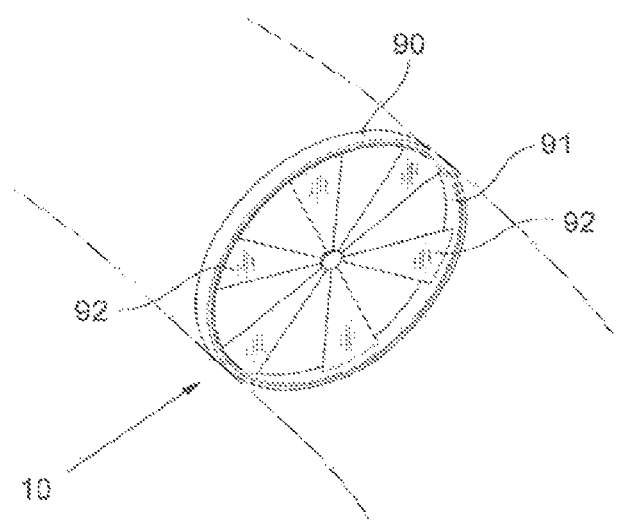
FIG. 31 is a view of an alternative embodiment of a cleaning apparatus.

Also other filters can be used in the cleaning device 10. One such filter is depicted in FIG. 31. The filter 90 in FIG. 31 comprises a rotating member 91 located in the flow passage way of the drainage device. The rotating member can be formed by a number of segments 92. Particles in the flow will caught by the segments and moved to the rim of the rotating member 91 where the particles can be effectively removed from the flow pathway of the drainage device. The cleaning device in FIG. 31 can be powered in the same manner as the cleaning device described above.

In FIG. 32 a general view of a patient having an implanted drainage apparatus as described herein. The apparatus comprises a first end of the drainage apparatus located in a treatment area 1. The apparatus further comprises a pump 100 adapted to move fluid from the treatment area 1 to a delivery area 3. The treatment area can be any area from which fluid is to be move including but not limited to the abdomen, the lungs and the brain. Similarly the delivery area can be any suitable delivery area within the body, including but not limited to the Urine bladder and the stomach.

The pump can be powered by an energy source 123 as described above. The energy source can be energized from outside the patient using a wireless energy transfer device. The energy transfer device can transfer energy in a way suitable such as by inductive energy using coils or ultra sonic energy transfer or by transmitting light through the skin of the patient. Also the fluid passageway from the treatment area to the delivery area can comprise a cleaning device 10 as described above. The cleaning device can in one embodiment be powered by a motor and the motor can then be supplied with energy from the energy source 123.

In FIG. 33 the drainage apparatus is shown in more detail. The view in FIG. 33 corresponds to the view in FIG. 32. However instead of showing the treatment areal, FIG. 33 shows and end member 4 of the tube located in the treatment area. As described above the end member 4 can be designed differently for different treatment areas. Different end members are described in more detail below.

Figure 34A:
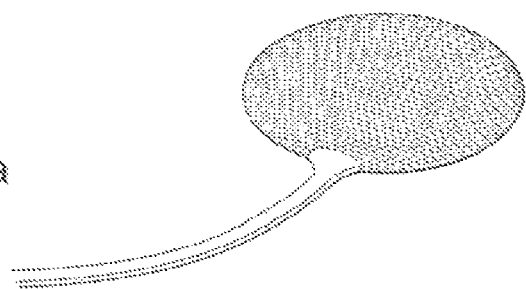
FIGS. 34a-34d are views of exemplary designs of tube ends for different treatment areas.
Figure 34B:
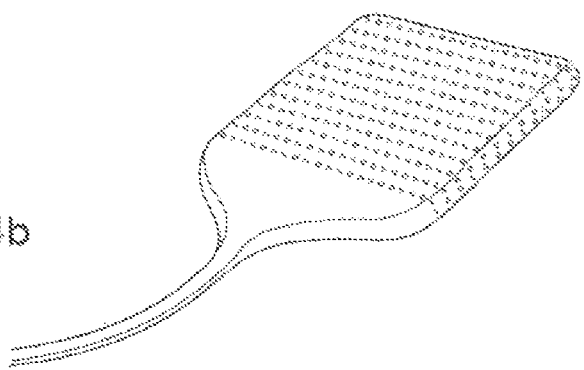

In FIGS. 34a-34d different exemplary designs of end members 4 are shown in more detail. Thus, a connecting tube for use in an implantable drainage device being adapted to move body fluid from one part of the body, herein termed treatment area, of a human or mammal patient is provided. A distal end of the connecting tube comprises in accordance with one embodiment a portion having a flat shape. Such an end portion can advantageously be used in the lungs when moving fluid from the lungs. The end portion can have an essential circular shape as is shown in FIG. 34a or have a polygonal shape as is shown in FIG. 34b.

Figure 34C:
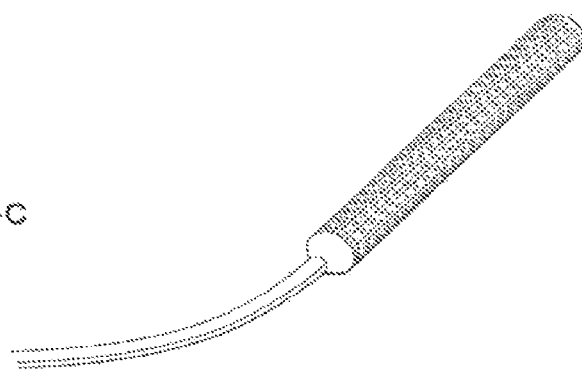
Figure 34D:
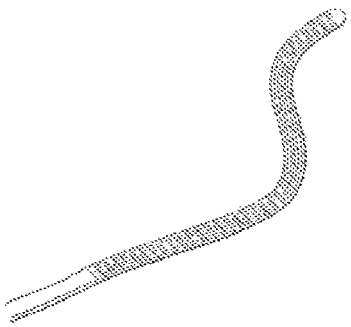

In accordance with one embodiment the distal end of the connecting tube can comprises a portion having a generally cylindrical shape as is shown in FIG. 34c. Such a shape can be preferred in applications where there is a risk that the tube end is sucked towards the wall of the treatment area. In FIG. 34d yet another embodiment is shown with a very flexible tube end that can be used as a versatile tube in that it combines advantages of a flat tube end and a cylindrical tube end at the expense of the disadvantages of being flexible.

The tube ends are provided with holes or formed by a netlike structure. The diameter of the hole can in accordance with one embodiment be in the range of 1-10 mm. The number of holes and the diameter can typically depend on the treatment. As a general rule more holes and larger holes will give a lower sucking force and vice versa. Thus, areas where a low sucking force is required such as in the lungs can be treated using a tube end having many and large holes in the tube end.

Figure 35:
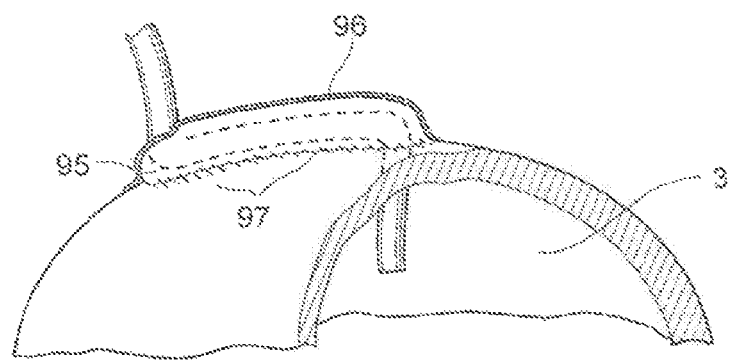
FIG. 35 is a view of a securing arrangement for securing a tube end in a bladder, such as the urine bladder.

In FIG. 35 a securing arrangement for securing a second end of a tube of the drainage device into the urine bladder is depicted. The arrangement comprises a tube end placed in the urine bladder 3 through a hole made in the wall of the urine bladder. On the outside the tube is led through a tunnel 95 formed by folding the outside wall of the urine bladder around the tube. The tunnel is secured around the tube by sutures 97 or similar. At the end of the tunnel a net structure 96 is tightly secured to the tube. The net structure has small diameter typically smaller than 0.5 mm. In any event the net structure has holes that will be small enough to be overgrown by tissue thereby providing a tight sealing so that no leakage occur. As stated above energy can be transferred in different manners from outside a patient into a implanted drain as described herein. In particular the energy can be transferred by means of an inductive energy transfer or by transmission using an ultrasonic energy transmission, or by transmission of energy using light.

Figure 36A:
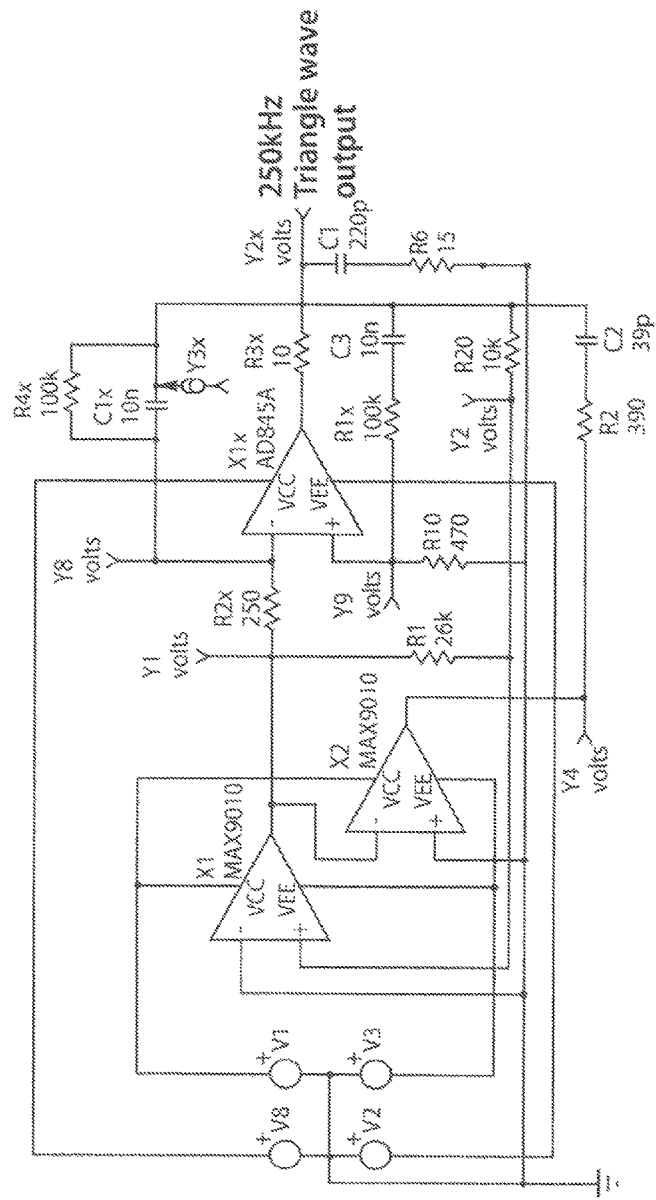
FIG. 36a is a circuit diagram showing an energy transfer amplifier, where the energy is transferred by ultrasonic waves.
Figure 36B:
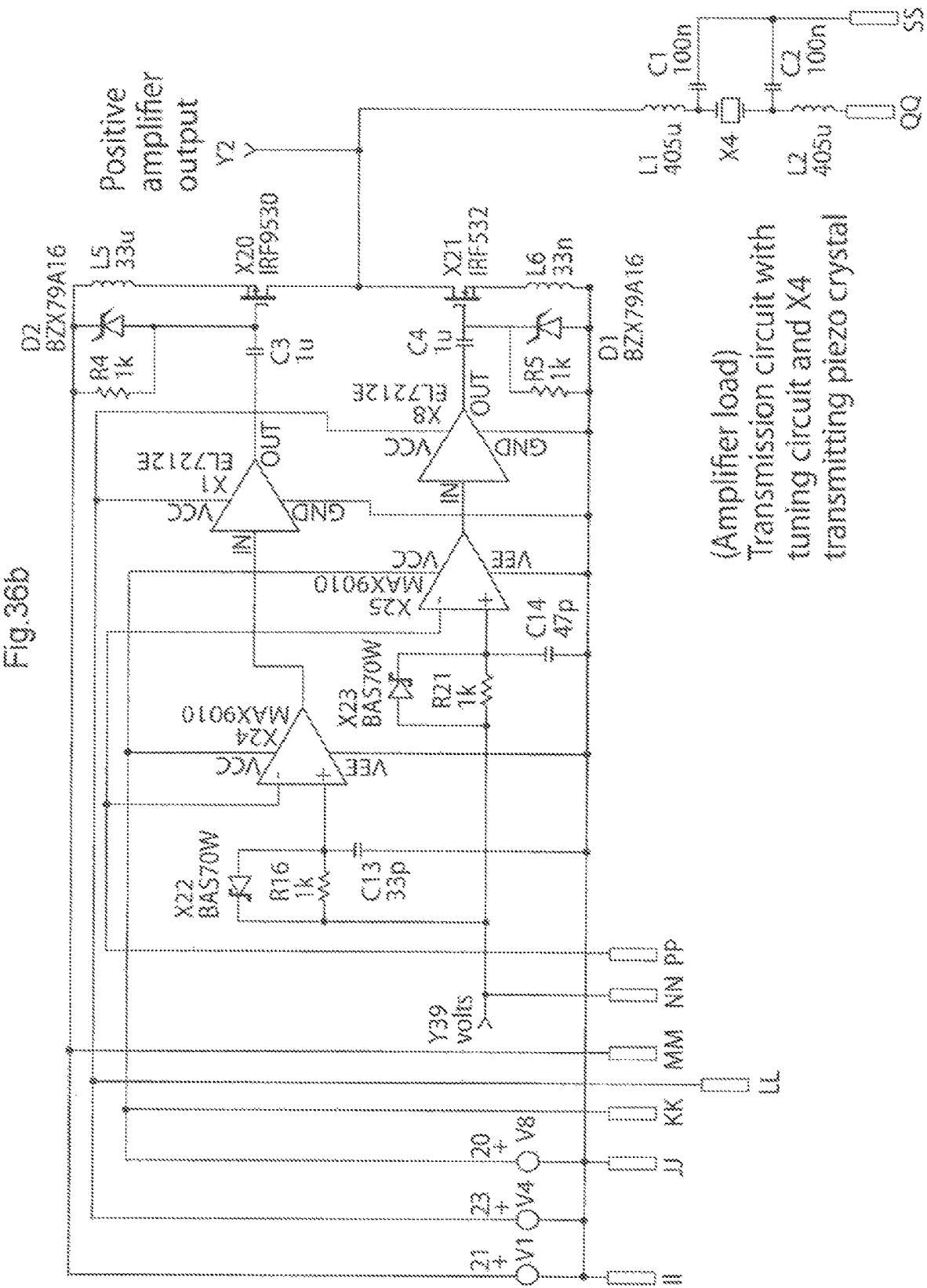
FIG. 36b is a circuit diagram showing further another embodiment of an amplifier.

FIG. 36*a* illustrates a triangle wave generator circuit, the output of which is connected as an input terminal of an amplifier used for transmitting energy using an ultrasonic energy transmission. In FIGS. 36*a* and 36*b* the symbols Y1, Y2, Y3 and so on symbolize test points within the circuit. The components in the circuit diagrams and their respective values are values that work in this particular implementation which of course is only one of an infinite number of possible design solutions.

FIG. 36*a* shows a circuit diagram containing most of an exemplary amplifier, in the lower left corner of FIG. 36*a* there is the LF input which is the input for the 25 kHz sine wave that should be amplified into a digital output signal. The LF-input there is the triangle wave input emanating from the Triangle schematic. To the right in the middle in the Core schematic there is the transmitting crystal, X4, connected to the differential digital outputs, positive and negative output, of the amplifier. The transmitting crystal X4 is in series with its associated tuning circuit components tuned to the sending frequency, which in this particular case is 25 kHz. FIGS. 36*c*-36*d* displays the relationship between the input and the output signal of the amplifier, in FIG. 36*c* Y25 is the input signal and Y2 is the positive digital output signal from the amplifier and in FIG. 36*d* Y13 is the negative digital output from the amplifier.

Figure 37:
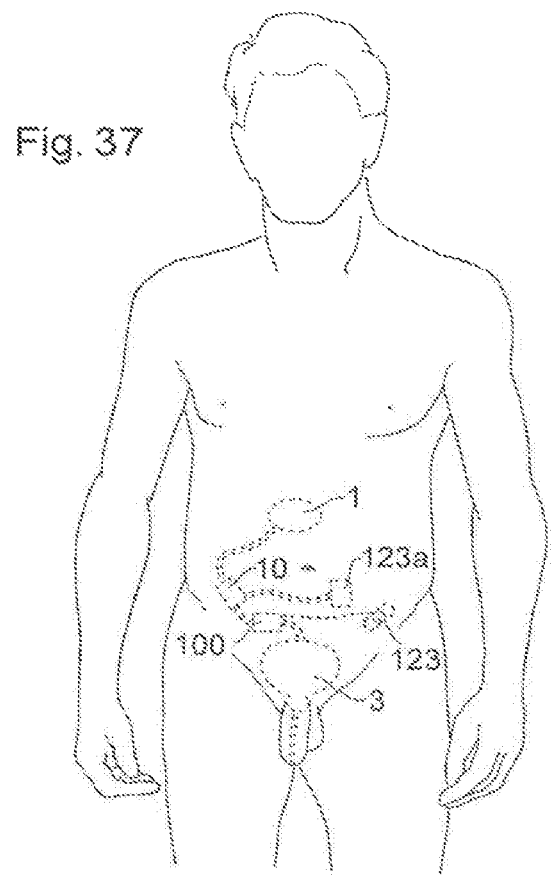
FIG. 37 is general view of an implanted drainage apparatus with a filter in a patient.

As described above the implanted drainage device can be powered by an internal power supply. The same power supply or another power supply can be used to provide energy the filter and or cleaning device 10 as described herein. In FIG. 37 a general view similar to the view in FIG. 32 is shown where the filter and the cleaning device 10 is connected to a power supply. The apparatus in FIG. 37 comprises a first end of the drainage apparatus located in a treatment area 1. The apparatus further comprises a pump 100 adapted to move fluid from the treatment area 1 to a delivery area 3. The treatment area can be any area from which fluid is to be move including but not limited to the abdomen, the lungs and the brain. Similarly the delivery area can be any suitable delivery area within the body, including but not limited to the Urine bladder and the stomach. The apparatus can as stated above further comprise a filter and or a cleaning device 10. The filter and or cleaning device 10 can be powered by an energy source 123*a* as described above. The energy source can be the same as the energy source 123 powering a pump, but can also be another energy source.

The energy source 123*a* can be energized from outside the patient using a wireless energy transfer device. The energy transfer device can transfer energy in a way suitable such as by inductive energy using coils or ultra sonic energy transfer or by transmitting light through the skin of the patient. Also the fluid passageway from the treatment area to the delivery area can comprise a cleaning device 10 as described above. The cleaning device can in one embodiment be powered by a motor and the motor can then be supplied with energy from the energy source 123*a*.

Figure 38:
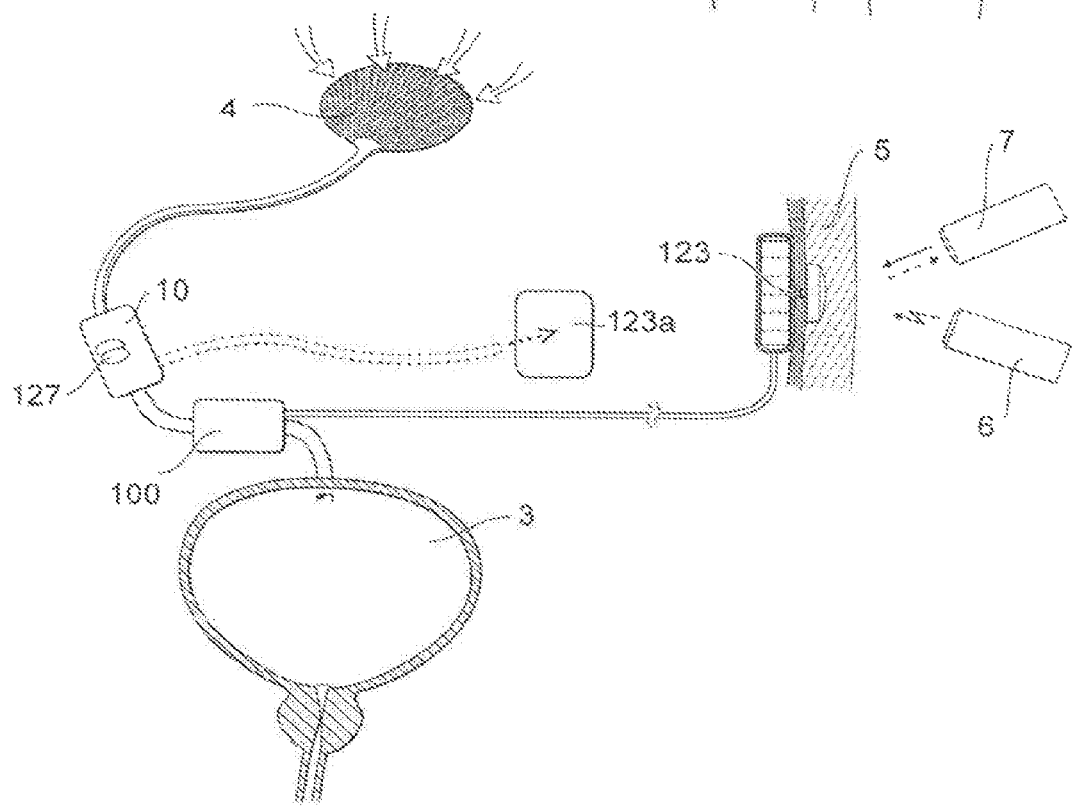
FIG. 38 is a detailed view of a powered filter.

In FIG. 38 the power supply to a filter and a cleaning device 10 is shown in more detail. The view in FIG. 38 corresponds to the view in FIG. 37. However instead of showing the treatment area 1, FIG. 38 shows and end member 4 of the tube located in the treatment area. As is shown in FIG. 38 the energy source 123 and 123*a* can be energized from outside the skin 5 of a patient by an external energy source 6. The energy source can also receive and transmit information to and from an external signaling device 7. The cleaning device can also be connected to changeable filter cassettes 127. In accordance with one embodiment a dirty filter of a cassette 127 is adapted to be replaced by a new filter of the cassette. The filter can also comprise a net structure.

In FIG. 39*a* a cassette 127 for holding filters is shown. The cassette 27 comprises a revolving cylinder 129 having segments 130 each holding a filter. The cylinder 129 is tightly sealed between two supports 131 holding the cylinder 129 in place and providing a tight sealing. The fluid passage way of an implantable drainage apparatus passes through the cassette 127. The cassette is driven by a motor 133 causing the cylinder 129 to revolve at suitable times. The motor is powered by a power supply 123*b*. The power supply can be a power supply like the power supplies 123 or 123*a*. In accordance with one embodiment the power supplies 123, 123*a* and 123*b* is the one and same power supply. As with the power supplies 123 and 123*a*, the power supply 123*b* can receive wireless energy in a suitable form, including but not limited to inductive energy ultrasonic energy, light energy or any other form of wireless energy set out above. The energy is supplied by an external wireless energy transmitter 6 adapted to transmit energy through the skin 5 of a patient having the cassette 127 implanted. The power supply 132*b* can also comprise a control unit as described above for controlling the revolving cassette 127. The control unit can provide feedback to the outside and receive input data from an external transceiver 7 in a manner similar to the control unit used in conjunction with control of the pump.

In FIG. 39*b* the cassette 127 is shown from the side with the supports 131 and the revolving cylinder spaced apart is a disassembled view.

Figure 40A:
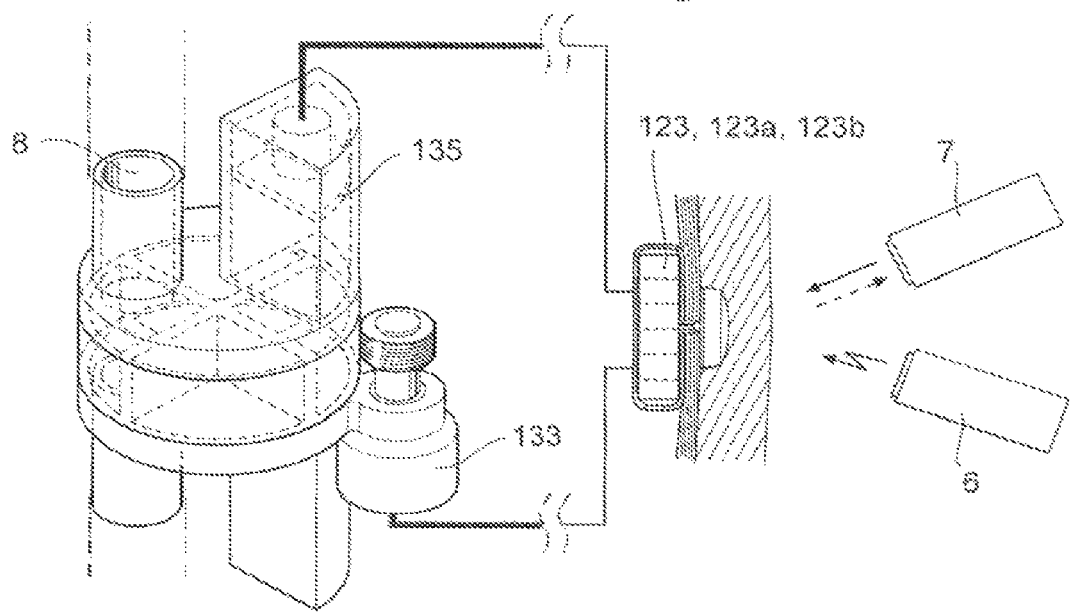
FIGS. 40a and 40b are views of a filter cassette.

In FIG. 40*a* an alternative embodiment of the cassette 127 is shown. The view in FIG. 39*a* is similar to the view in FIG. 39*a*. In the embodiment in FIG. 40*a* a magazine 135 having a number of cylinders 129 stored therein is provided. Hereby a cylinder 129 can by replaced by shifting the cylinders in the magazine 135. In one embodiment the cylinders are shifted by pressurized air.

Figure 40B:
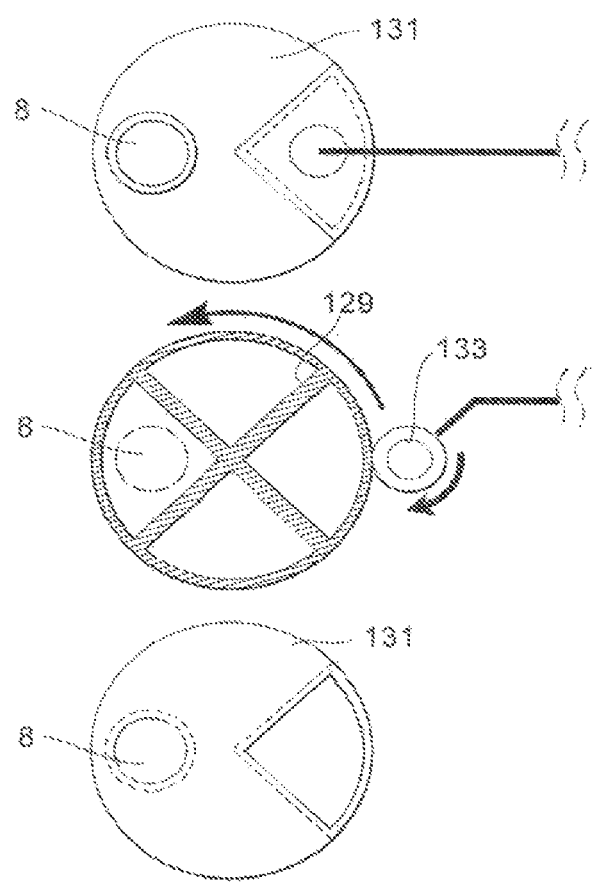

In FIG. 40*b* the cassette 127 is shown from the side with the supports 131 and the revolving cylinder spaced apart is a disassembled view.

Please note that any embodiment or part of embodiment or feature or method or associated system or part of system described herein may be combined in any combination.

The invention claimed is:

1. A filtering device for removing particles from a bodily fluid of a patient, the filtering device being implantable in the patient's body and comprising:
   a tube forming a main fluid passageway for bodily fluid, through which the bodily fluid of the patient passes when the tube is implanted in the patient,
   a filter connected to the tube and, when in use, arranged for filtering the bodily fluid passing through said main fluid passageway and collecting said particles to be removed passing through the tube, and
   a filter cleaning device for cleaning the filter by moving particles collected by the filter out of the fluid passageway, wherein the filter cleaning device is adapted to replace a filter in the fluid passageway with a second filter, thereby moving the particles collected by the first filter out of the fluid passageway.

2. The device according to claim 1, further comprising additional replacement filters adapted to replace the first filter, when the first filter is moved from said fluid passageway.

3. The device according to claim 1, further comprising an operation device adapted to operate the cleaning device to exchange the first filter.

4. The system according to claim 3, wherein the operation device for exchanging the first filter comprises a motor or a pump.

5. The device according to claim 1, wherein the cleaning device comprises a rotating cassette (127) adapted to rotate the first filter out from the fluid passageway.

6. The device according to claim 3, wherein the operation device is adapted to operate the cleaning device to clean the exchanged first filter, for being ready for later reinstallation in the fluid passageway.

7. The device according to claim 1, wherein the cleaning device is adapted to slice, push or scratch away any particles from the filter or by sucking away any particles from the first filter, when placed in the fluid passageway or after being moved away from the fluid passageway.

8. The device according to claim 1, adapted to place the particles in at least one of: a collecting volume adapted to collect particles that have been cleaned from the first filter, and a free space in the patient's body, wherein the first filter is adapted to take into account a fibrotic capsula covering the cleaning device when implanted.

9. The device according to claim 1 comprising a sensor adapted to sense a functional parameter of the of the device.

10. The device according to claim 9, comprising an internal control unit acting in response to the parameter sensed by the sensor, the device further comprising an operation device for operating the cleaning device, wherein the internal control unit controls the operation device to operate the cleaning device in response to the sensor sensing a parameter related to the accumulation of particles in the filter.

11. The device according to claim 9, wherein accumulation of particles in the first filter is sensed with at least one of: a visualizing light sensor, a sensor measuring an electrical parameter, a sensor measuring a fluid flow, a pressure sensor, a sensor measuring a pressure difference before and after the first filter, or any other kind of sensor.

12. The device according to claim 9, comprising a feedback device for sending information from inside the patient's body to the outside thereof to give feedback information related to a functional parameter of the filtering device in response to the sensor sensing a parameter related to the accumulation of particles,
   and/or a physical parameter of the patient in response to the sensor sensing a parameter related to the accumulation of particles.

13. The device according to claim 9, comprising at least one of: an energy source adapted to power energy consuming parts of the filtering device and a wireless energy transmitter for non-invasively energizing energy consuming parts of the filtering device.

14. The device according to claim 9, comprising a wireless remote control for non-invasively regulating a function of the filtering device.

15. The device according to claim 1 comprising a sensor adapted to sense a physical parameter of the patient.

16. The device according to claim 15, comprising an internal control unit acting in response to the parameter sensed by the sensor, the device further comprising an operation device for operating the cleaning device, wherein the internal control unit controls the operation device to operate the cleaning device in response to the sensor sensing a parameter related to the accumulation of particles in the filter.

17. The device according to claim 15, wherein accumulation of particles in the first filter is sensed with at least one of: a visualizing light sensor, a sensor measuring an electrical parameter, a sensor measuring a fluid flow, a pressure sensor, a sensor measuring a pressure difference before and after the first filter, or any other kind of sensor.

18. The device according to claim 15, comprising a feedback device for sending information from inside the patient's body to the outside thereof to give feedback information related to a physical parameter of the patient in response to the sensor sensing a parameter related to the accumulation of particles.

19. The device according to claim 15, comprising at least one of: an energy source adapted to power energy consuming parts of the filtering device, a wireless energy transmitter for non-invasively energizing energy consuming parts of the filtering device.

20. The device according to claim 15, comprising a wireless remote control for non-invasively regulating a function of the filtering device.

* * * * *